US012595295B2

(12) United States Patent
Soto et al.

(10) Patent No.: US 12,595,295 B2
(45) Date of Patent: Apr. 7, 2026

(54) DOSING REGIMES FOR TREATMENT OF SYNUCLEINOPATHIES

(71) Applicants: Prothena Biosciences Limited, Dublin (IE); F. Hoffmann-La Roche AG, Basel (CH)

(72) Inventors: Jay Soto, San Francisco, CA (US); Daniel Keith Ness, San Mateo, CA (US); Martin Koller, Rancho Santa Fe, CA (US); Diane Mould, Fort Myers, FL (US); Frank Boess, Basel (CH); Meret Martin-Facklam, Basel (CH); Valerie Cosson, Basel (CH); Hans Peter Grimm, Basel (CH); Ronald Gieschke, Basel (CH); Sara Belli, Basel (CH); Silke Weber, Basel (CH)

(73) Assignees: Prothena Biosciences Limited, Dublin (IE); Hoffmann-La Roche, Inc., Little Falls, NY (US)

( * ) Notice: Subject to any disclaimer, the term of this patent is extended or adjusted under 35 U.S.C. 154(b) by 0 days.

(21) Appl. No.: 16/936,457

(22) Filed: Jul. 23, 2020

(65) Prior Publication Data

US 2021/0079103 A1      Mar. 18, 2021

Related U.S. Application Data

(63) Continuation of application No. 16/145,618, filed on Sep. 28, 2018, now abandoned.

(60) Provisional application No. 62/564,992, filed on Sep. 28, 2017.

(51) Int. Cl.
| | |
|---|---|
| *C07K 16/18* | (2006.01) |
| *A61B 5/00* | (2006.01) |
| *A61B 5/11* | (2006.01) |
| *A61K 9/00* | (2006.01) |
| *A61K 31/198* | (2006.01) |
| *A61K 39/00* | (2006.01) |
| *A61P 25/16* | (2006.01) |
| *A61P 25/28* | (2006.01) |
| *C07K 16/28* | (2006.01) |

(52) U.S. Cl.
CPC ............ *C07K 16/18* (2013.01); *A61B 5/0004* (2013.01); *A61B 5/4848* (2013.01); *A61K 9/0019* (2013.01); *A61K 31/198* (2013.01); *A61P 25/16* (2018.01); *A61P 25/28* (2018.01); *C07K 16/2857* (2013.01); *A61B 5/11* (2013.01); *A61B 5/1101* (2013.01); *A61B 5/4082* (2013.01); *A61K 2039/505* (2013.01); *A61K 2039/545* (2013.01)

(58) Field of Classification Search
CPC ....... A61B 5/4848; A61B 5/0004; A61B 5/11; A61B 5/1101; A61B 5/4082; A61K 9/0019; A61K 31/198; A61K 2039/505; A61K 2039/545; A61K 39/3955; A61P 25/16; A61P 25/28; C07K 16/18; C07K 2317/22
See application file for complete search history.

(56) References Cited

U.S. PATENT DOCUMENTS

| | | | |
|---|---|---|---|
| 8,940,276 B2 | 1/2015 | Weihofen et al. | |
| 9,580,493 B2 | 2/2017 | Weihofen et al. | |
| 2005/0240086 A1 | 10/2005 | Akay | |
| 2006/0122472 A1 | 6/2006 | Pullman | |
| 2007/0092889 A1 | 4/2007 | Cox et al. | |
| 2008/0014194 A1 | 1/2008 | Schenk et al. | |
| 2010/0076348 A1 | 3/2010 | Mcnames et al. | |
| 2011/0230513 A1 | 9/2011 | Lamensdorf et al. | |
| 2013/0123666 A1 | 5/2013 | Giuffrida et al. | |
| 2015/0073310 A1 | 3/2015 | Pracar et al. | |
| 2015/0079074 A1* | 3/2015 | Garidel .................. C07K 16/18 |
| | | | 530/387.3 |
| 2016/0108113 A1* | 4/2016 | Ayalon .................... A61P 43/00 |
| | | | 435/69.6 |
| 2018/0126158 A1 | 5/2018 | Perez et al. | |
| 2022/0031561 A1 | 2/2022 | Zhao | |
| 2022/0098291 A1 | 3/2022 | Pagano et al. | |

FOREIGN PATENT DOCUMENTS

| | | |
|---|---|---|
| JP | A-2009-291379 | 12/2009 |
| WO | WO 2006/020581 | 2/2006 |
| WO | WO 2012/177972 | 12/2012 |
| WO | WO 2015/001504 | 1/2015 |
| WO | WO 2015/075635 | 5/2015 |
| WO | WO 2015/118534 | 8/2015 |
| WO | WO 2018/178950 | 10/2018 |

OTHER PUBLICATIONS

Yang K et al. Objective and quantitative assessment of motor function in Parkinson's disease—from the perspective of practical applications. Ann Transl Med. Mar. 2016, 4(5): 90; 8 pages. (Year: 2016).*
Ashraf et al., "Constipation in Parkinson's disease: objective assessment and response to psyllium." Movement Disorders 12(6):946-51 (Nov. 1997).

(Continued)

*Primary Examiner* — Kimberly Ballard

(74) *Attorney, Agent, or Firm* — McDonnell Boehnen Hulbert & Berghoff LLP

(57) ABSTRACT

The invention provides dosage regimes for treatment of synucleinopathies. In one regime, a subject receives 3000-5000 mg of an antibody intravenously every 3-5 weeks. In another regime, a subject receives 1300-1700 mg of an antibody intravenously every 3-5 weeks.

13 Claims, No Drawings

Specification includes a Sequence Listing.

(56)                    References Cited

OTHER PUBLICATIONS

Cheng et al., "Human activity recognition from sensor-based large-scale continuous monitoring of Parkinson's disease patients." CHASE '17 Proceedings of the Second IEEE/ACM International Conference on Connected Health: Applications, Systems and Engineering Technologies, Jul. 17-19, 2017; Philadelphia, PA, pp. 249-250 (2017).

Conway et al., "Acceleration of oligomerization, not fibrillization, is a shared property of both alpha-synuclein mutations linked to early-onset Parkinson's disease: implications for pathogenesis and therapy." Proc Natl Acad Sci USA, 97(2):571-76 (Jan. 2000).

Feany & Bender, "A *Drosophila* model of Parkinson's disease." Nature 404(677):394-98 (Mar. 2000).

Galasko et al., "Clinical-neuropathological correlations in Alzheimer's disease and related dementias." Arch. Neurol. 51(9):888-95 (Sep. 1994).

Krüger et al., "Ala30Pro mutation in the gene encoding alpha-synuclein in Parkinson's disease." Nature Gen. 18(2):106-8 (Feb. 1998).

Lipsmeier et al., "Successful passive monitoring of early-stage Parkinson's disease patient mobility in Phase I RG7935/PRX002 clinical trial with smartphone sensors." Mov Disord. Abstracts of the 21st International Congress of Parkinson's Disease and Movement Disorders. 32(suppl 2):S1-S1079, Abstract # 541 (Jun. 6, 2017).

Masliah et al., "Dopaminergic loss and inclusion body formation in alpha-synuclein mice: implications for neurodegenerative disorders." Science 287(5456):1265-9 (Feb. 2000).

Masliah et al., "Passive immunization reduces behavioral and neuropathological deficits in an alpha-synuclein transgenic model of Lewy body disease." PLoS ONE 6(4):e19338 (Apr. 2011).

Mckeith et al., "Consensus guidelines for the clinical and pathologic diagnosis of dementia with Lewy bodies (DLB): report of the consortium on DLB international workshop." Neurology, 47(5):1113-24 (Nov. 1996).

Ondo et al., "Placebo-controlled trial of lubiprostone for constipation associated with Parkinson disease." Neurology, 78(21):1650-54 (May 2012; Epub May 9, 2012).

Ordóñez & Roggen, "Deep Convolutional and LSTM Recurrent Neural Networks for Multimodal Wearable Activity Recognition." Sensors, 16(1):E115 (Jan. 2016).

Polymeropoulos et al., "Mutation in the alpha-synuclein gene identified in families with Parkinson's disease." Science 276(5321):2045-7 (Jun. 1997).

Rai et al., "Zee: zero-effort crowdsourcing for indoor localization." Mobicom '12 Proceedings of the 18th annual International conference on Mobile computing and networking; pp. 293-304, Istanbul, Turkey (Aug. 22-26, 2012).

Spillantini et al., "Alpha-synuclein in Lewy bodies." Nature, 388(6645):839-40 (Aug. 1997).

Stisen et al., "Smart Devices are Different: Assessing and MitigatingMobile Sensing Heterogeneities for Activity Recognition." SenSys '15 Proceedings of the 13th ACM Conference on Embedded Networked Sensor Systems, Seoul, Korea, pp. 127-140, (Nov. 1-4, 2015).

Takeda et al., "Abnormal accumulation of NACP/alpha-synuclein in neurodegenerative disorders." Am. J. Pathol. 152(2):367-72 (Feb. 1998).

Ueda et al., "Molecular cloning of cDNA encoding an unrecognized component of amyloid in Alzheimer disease." Proc. Natl. Acad. Sci. USA, 90(23):11282-6 (Dec. 1993).

Wakabayashi et al., "NACP, a presynaptic protein, immunoreactivity in Lewy bodies in Parkinson's disease." Neurosci. Lett. 239(1):45-8 (Dec. 1997).

Weiss & Lockhart, "The Impact of Personalization on Smartphone-Based Activity Recognition." In Papers from the AAAI-12 Work-shop on Activity Context Representation: Techniques and Languages, AAAI Technical Report WS-12-05, Toronto, Canada, 98-104, (2012).

Zijlstra et al., "Sit-stand and stand-sit transitions in older adults and patients with Parkinson's disease: event detection based on motion sensors versus force plates." J. Neuroengineering and Rehabilitation 9:75 (Oct. 2012).

Leiber et al., Motion Sensors to Assess and Monitor Medical and Surgical Management of Parkinson Disease. World Neurosurg. Aug. 2015;84(2):561-6. doi: 10.1016/j.wneu.2015.03.024. Epub Mar. 28, 2015.

Pagano, G., et al., "Trial of Prasinezumab in Early-State Parkinson's Disease", The New England Journal of Medicine, 387:421-32 (2022).

Pagano, G., et al, "Pasadena: A phase 2 study to evaluate the safety and efficacy of prasinezumab in early Parkinson's disease: Part 1 Week-52 results", International Parkinson and Movement Disorder Society Virtual Congress, Sep. 14, 2020.

Beach et al., "Arizona Parkinson's Disease Consortium. Unified staging system for Lewy body disorders: correlation with nigrostriatal degeneration, cognitive impairment and motor dysfunction." Acta Neuropathol. 117:613-34 (2009).

Bhidayasiri et al., "Different diagnostic criteria for Parkinson disease: What are the pitfalls?" J Neural Transm. 120:619-25 (2013).

Brettschneider et al., "Spreading of pathology in Neurodegenerative diseases: a focus on human studies." Nat Rev Neurosci. 16:109-120 (2015).

Cheng et al., "Clinical progression in Parkinson disease and the neurobiology of axons." Ann Neurol. 67:715-25 (2010).

Clinical Trial No. NCT02095171 "Single Ascending Dose Study of PRX002 in Healthy Subjects" last updated Feb. 10, 2015, pp. 1-10.

Clinical Trial No. NCT03100149 "A Study to Evaluate the Efficacy of Prasinezumab (RO7046015/PRX002) in Participants With Early Parkinson's Disease (PASADENA)." Study registration posted Apr. 4, 2017. pp. 1-13.

De Lau et al. "Prognosis of Parkinson disease: risk of dementia and mortality: the Rotterdam Study." Arch Neurol. 62:1265-69 (2005).

Dehay et al., "Targeting α-synuclein for treatment of Parkinson's disease mechanistic and therapeutic considerations." Lancet Neurol. 14:855-66 (2015).

Del Din et al., "Free-living gait characteristics in ageing and Parkinson's disease: impact of environment and ambulatory bout length." J. Neuroengineering and Rehabilitation, 13:46 (2016).

Desplats et al., "Inclusion formation and neuronal cell death through neuron-to-neuron transmission of alpha-synuclein." PNAS 106:13010-13015 (2009).

Dunning et al., "What's to like about the prion-like hypothesis for the spreading of aggregated alpha-synuclein in Parkinson disease?" Prion 7:92-97 (2013).

Fereshtehnejad et al., "New Clinical Subtypes of Parkinson Disease and Their Longitudinal progression: A Prospective Cohort Comparison With Other Phenotypes." JAMA Neurol. 72:863-873 (2015).

Freundt et al., "Neuron-to-Neuron transmission of α-synuclein fibrils through axonal transport." Ann Neurol. 72:517-524 (2012).

Games et al. Reducing C-terminal-truncated alpha-synuclein by immunotherapy attenuates neurodegeneration and propagation in Parkinson's disease-like models. J Neurosci. 34:9441-54 (2014).

Gelb et al., "Diagnostic Criteria for Parkinson Disease." Arch Neurol. 56:33-39 (1999).

Gen Bank, Accession No. P37840. Oct. 1, 1994, www.ncbi.nlm.nih.gov. (Year record was published: 1994).

Gibb & Lees, "The relevance of Lewy body to the pathogenesis of idiopathic Parkinson's disease." J Neurol Neurosurg Psych. 51:745-52 (1988).

Goetz et al. "Movement Disorder Society-sponsored revision of the Unified Parkinson's Disease Rating Scale (MDS-UPDRS): scale presentation and clinimetric testing results." Mov Disord 23:2129-70 (2008).

Jankovic et al. "Safety and tolerability of multiple ascending doses of PRX002/RG7935, an anti-alpha-synuclein monoclonal antibody, in patients with Parkinson Disease: A randomized clinical trial." JAMA Neurol 75:1206-14 (2018).

(56)                    References Cited

OTHER PUBLICATIONS

Kowal et al. "The current and projected economic burden of Parkinson's disease in the United States." Mov Disord 28:311-18 (2013).

Lang & Espay, "Disease Modification in Parkinson's Disease Current Approaches, Challenges, and Future Considerations." Mov Disord. 33:660-77 (2018).

Lee et al., "Intravesicular localization and exocytosis of alpha-synuclein and its aggregates." J Neurosci. 25:6016-24 (2005).

Lipsmeier et al. "Evaluation of smartphone-based testing to generate exploratory outcome measures in a phase 1 Parkinson's disease clinical trial: Remote PD Testing with Smartphones." Movement Disorders. Apr. 27, 2018 https://doi.org/10.1002/mds.27376.

Luk et al., "Pathological α-synuclein transmission initiates Parkinson-like neurodegeneration in nontransgenic mice." Science. 338:949-53 (2012).

Marek et al. "Longitudinal follow-up of SWEDD subjects in the PRECEPT Study." Neurology 82:1791-97 (2014).

Masliah et al., "Effects of alpha-synuclein immunization in a mouse model of Parkinson's disease." Neuron. 46:857-68 (2005).

Masuda-Suzukake et al., "Prion-like spreading of pathological α-synuclein in brain." Brain. 136:1128-38 (2013).

National Institute of Neurological Disorders and Stroke (NINDS) "Parkinson's Disease Information Page." Accessed Feb. 3, 2022, pp. 1-7.

Parkinson's Foundation. www.parkinson.org/Understanding-Parkinsons/Statistics. Accessed Feb. 3, 2022, pp. 1-9.

Postuma et al. "The new definition and diagnostic criteria of Parkinson's disease." Lancet Neurol 15(6):546-48 (2016).

Schenk et al. "First-in-human assessment of PRX002, an anti-alpha-synuclein monoclonal antibody, in healthy volunteers." Mov Disord 32:211-18 (2017).

Shankar et al. "Assessment and reporting of the clinical immunogenicity of therapeutic proteins and peptides—harmonized terminology and tactical recommendations." The AAPS Journal 16 (2014).

Simuni et al. "Longitudinal Change of Clinical and Biological Measures in Early Parkinson's Disease: Parkinson's Progression Markers Initiative Cohort: Early PD and MDS-UPDRS and Dat Binding Change." Mov Disord. 33:771-82 (2018).

Spencer et al., "Anti-α-synuclein immunotherapy reduces α-synuclein propagation in the axon and degeneration in combines viral vector and transgenic model of synucleinopathy." Acta Neuropathol Commun. 5:7 (2017).

Spillantini et al., "alpha-Synuclein in filamentous inclusions of Lewy bodies from Parksinon's disease and dementia with lewy bodies." Proc Natl Acad Sci USA. 95:6469-73 (1998).

Sprenger "Management of Motor and Non-Motor Symptoms in Parkinson's Disease." CNS Drugs 27:259-72 (2013).

The MDS-sponsored Revision of the Unified Parkinson's Disease Rating Scale, International Parkinson and Movement Disorder Society, 2008, pp. 1-33. last updated Aug. 2019.

Volpicelli-Daley et al., "Exogenous α-synuclein fibrils induce Lewy body pathology leading to synaptic dysfunction and neuron death." Neuron. 72:57-71 (2011).

Weintraub et al., "Parkinson's Disease: The Quintessential Neuropsychiatric Disorder." Mov Disord 26:1022-31 (2011).

Belousov et al. "Clinical pharmacokinetics. Practice of drug dosing" M. Litterra p. 288 (2005).

Kharkevich et al. "Pharmacology: Textbook—9th ed., revised, enlarged and corrected" Moscow: GEOTAR-Media p. 736 (2006).

Office Action of Russian Patent Application 2023107315 issued Feb. 10, 2025, 6 pages (attached to show relevance of Belousov et al and Kharkevich et al).

* cited by examiner

DOSING REGIMES FOR TREATMENT OF SYNUCLEINOPATHIES

SEQUENCE LISTING

A sequence listing, comprising SEQ ID NOs: 1-151, is attached and incorporated by reference in its entirety. The listing, named 502165SEQLIST.txt, was created on Aug. 31, 2017, in ASCII format and is 127,151 bytes in size.

BACKGROUND

Lewy body diseases (LBDs) are characterized by degeneration of the dopaminergic system, motor alterations, cognitive impairment, and formation of Lewy bodies (LBs) and/or Lewy neurites. (McKeith et al., Neurology (1996) 47:1113-24). Lewy Body disease include Parkinson's disease (including idiopathic Parkinson's disease), and Dementia with Lewy Bodies (DLB). Lewy body diseases are a common cause for movement disorders and cognitive deterioration in the aging population (Galasko et al., Arch. Neurol. (1994) 51:888-95). Constipation is another common symptom of subjects with Lewy body disease (Ondo et al., Neurology 2012; 78; 1650-1654; Ashraf et al., Movement Disorders 12, 946-951 (1997)).

Alpha-synuclein is a protein that is normally associated with synapses and is believed to play a role in neural plasticity, learning and memory. Alpha-synuclein is also implicated with a central role in pathogenesis of Lewy body disease. The protein can aggregate to form insoluble fibrils in pathological conditions. For example, alpha-synuclein accumulates in LBs (Spillantini et al., Nature (1997) 388: 839-40; Takeda et al., J. Pathol. (1998) 152:367-72; Wakabayashi et al., Neurosci. Lett. (1997) 239:45-8). Mutations in the alpha-synuclein gene co-segregate with rare familial forms of parkinsonism (Kruger et al., Nature Gen. (1998) 18:106-8; Polymeropoulos, et al., Science (1997) 276:2045-7). Over expression of alpha-synuclein in transgenic mice (Masliah et al., Science (2000) 287:1265-9) and *Drosophila* (Feany et al., Nature (2000) 404:394-8) mimics several pathological aspects of Lewy body disease. Soluble oligomers of alpha-synuclein may be neurotoxic (Conway et al., Proc Natl Acad Sci USA (2000) 97:571-576. The accumulation of alpha-synuclein with similar morphological and neurological alterations in species and animal models as diverse as humans, mice, and flies suggests that this molecule contributes to the development of Lewy body disease.

Immunotherapy directed against alpha-synuclein has been reported to reduce alpha-synuclein deposits and behavioral symptoms in mouse models of Lewy body disease (Masliah et al., PLoS ONE 6(4): e19338. doi:10.1371/journal. pone.0019338).

SUMMARY OF THE CLAIMED INVENTION

In one aspect, the invention provides a method of treating or effecting prophylaxis of a subject having or at risk of a synucleinopathy comprising intravenously administering to the subject a dose of 3000-5000 mg of an antibody against alpha-synuclein at intervals of 3-5 weeks, or administering another regime that delivers the antibody to the subject with substantially the same area under the curve. In some such methods the dose is 3500-4500 mg.

In some such methods, the antibody is administered to a plurality of subjects having or at risk of the synucleinopathy wherein subjects receive either one or two fixed doses. In some such methods, subjects with a weight less than 65 kg receive a dose of 3500 mg antibody and subjects with a weight greater or equal to 65 kg receive a dose of 4500 mg.

In some such methods, the dose of 45-75 mg/kg. In some such methods, the dose is 50-70 mg/kg.

In some such methods, the intervals are 28 days. In some such methods, the subject receives at least six doses of the antibody at the intervals of 3-5 weeks. In some such methods, the subject receives at least 12 doses of the antibody at the intervals of 3-5 weeks. In some such methods, the subject receives at least 18 doses of the antibody at the intervals of 3-5 weeks. In some such methods, the interval is 4 weeks. In some such methods, the subject receives the antibody every 4 weeks for at least 52 weeks.

Some such methods further comprise monitoring the subject for a change in movement, cognitive deficit, autonomic dysfunction, gastrointestinal dysfunction, visual hallucination or a psychological symptom.

In some such methods, the monitoring comprises
  (a) providing a subject with a mobile device programmed to receive and transmit data acquired from sensors internal and/or external to the device relating to movement deficits of a subject having or suspected of having a synucleinopathy, whereafter the subject undergoes a series of movements to reveal movement deficits, if present, and the internal or external sensors of the device acquire data relating to the movements;
  (b) collecting data transmitted from the mobile device; and
  (c) comparing the data acquired from the subjects with control data to assess presence or extent of movement deficits in the subject.

In some such methods, the mobile device is programmed to receive and transmit data from at least two external sensors attached to upper and lower limbs of the subject. In some such methods, the mobile device acquires data from sensors on the upper and lower limbs of the subject. In some such methods, the mobile device is carried by the subject and acquires data from an internal sensor. In some such methods, the series of movements includes tapping the device, sitting and standing. In some such methods, the monitoring indicates a reduced movement deficit or a reduced cognitive deficit responsive to administering the antibody.

In some such methods, the antibody binds within residues 115-130 of alpha synuclein.

In some such methods, the antibody binds with residues 118-126 of alpha synuclein.

In some such methods, the antibody binds within residues 117-123 of alpha synuclein. In some such methods, the antibody is NI-202.21D11. In some such methods, the antibody comprises three heavy CDRs designated SEQ ID NOs:139-141 respectively and three light chain CDRs designated SEQ ID NOs: 143-145 respectively. In some such methods, the antibody comprises a heavy chain variable region designated SEQ ID NO:138 and a light chain variable region designated SEQ ID NO:142.

In some such methods, the antibody comprises the three light chain Kabat CDRs of SEQ ID NO:5 and the three heavy chain Kabat CDRs of SEQ ID NO:10. In some such methods, the antibody comprises a heavy chain variable region of any of SEQ ID NOs:8-11 and a light chain variable region of any of SEQ ID NO:3-5, preferably wherein the heavy chain variable region is of SEQ ID NO:10 and a light chain variable region of SEQ ID NO:5.

In some such methods, the antibody is of human IgG1 isotype. In some such methods, the antibody comprises a heavy chain constant region of SEQ ID NO:35 provided the C-terminal lysine of SEQ ID NO:35 may be absent and a light chain constant region of SEQ ID NO:30. In some such methods, the antibody comprises a heavy chain constant region of SEQ ID NO:35 provided the C-terminal lysine of SEQ ID NO:35 may be absent and a light chain constant region of SEQ ID NO:13.

In some such methods, the antibody is 9E4. In some such methods, the antibody comprises three heavy CDRs designated SEQ ID NOs: 146-148 respectively and three light chain CDRs designated SEQ ID NOs: 149-151 respectively. In some such methods, the antibody comprises a heavy chain designated SEQ ID NO:37 and a light chain designated SEQ ID NO:32, wherein the C-terminal lysine of SEQ ID NO:37 may be absent.

In some such methods, the antibody binds within residues 1-20 of alpha-synuclein. In some such methods, the antibody binds with residues 4-15 of alpha-synuclein.

In some such methods, the antibody is NI-202.12F4. In some such methods, the antibody comprises three heavy CDRs designated SEQ ID NOs:131-133 respectively and three light chain CDRs designated SEQ ID NOs: 135-137 respectively. In some such methods, the antibody comprises a heavy chain variable region designated SEQ ID NO:130 and a light chain variable region designated SEQ ID NO:134.

In some such methods, the subject has a weight less than 65 kg and is administered a dose of 3500 mg antibody every 4 weeks.

In some such methods, the administration of the antibody within the range of 3000-5000 mg is preceded by administering a loading dose of 2000 mg of the antibody and optionally uptitration at one or more subsequent dose at greater or equal to 2000 mg but less than 3500 mg until a dose of 3500 mg is reached, all doses being separated by intervals of 3-5 weeks.

In some such methods, the 3500 mg dose is administered in the next interval after the 2000 mg dose. In some such methods, the dose is gradually increased over several intervals prior to administration of the 3500 mg dose. In some such methods, the subject has a weight greater than 65 kg and is administered a dose of 4500 mg antibody every 4 weeks.

In some such methods, the antibody is administered at 4500 mg preceded by administration of a loading dose of 2000 mg of the antibody and optionally uptitration with one or more subsequent doses of greater than or equal to 2000 mg but less than 4500 mg until a dose of 4500 mg is reached with all doses being separated by intervals of 3-5 weeks.

In some such methods, the 4500 mg dose is administered in the next interval after the 2000 mg dose. In some such methods, the dose is gradually increased over several intervals prior to administration of the 4500 mg dose.

Some such methods further comprise monitoring the subject for a change in movement, cognitive deficit autonomic dysfunction, gastrointestinal dysfunction, visual hallucination or a psychological symptom.

In some such methods, the monitoring comprises (a) providing a subject with a mobile device programmed to receive and transmit data acquired from sensors internal and/or external to the device relating to movement deficits of a subject having or suspected of having a synucleinopathy, whereafter the subject undergoes a series of movements to reveal movement deficits, if present, and the internal or external sensors of the device acquire data relating to the movements;

(b) collecting data transmitted from the mobile device; and (c) comparing the data acquired from the subjects with control data to assess presence or extent of movement deficits in the subject.

In some such methods, the mobile device is programmed to receive and transmit data from at least two external sensors attached to upper and lower limbs of the subject. In some such methods, the mobile device acquires data from sensors on the upper and lower limbs of the subject. In some such methods, the mobile device is carried by the subject and acquires data from an internal sensor. In some such methods, the series of movements includes tapping the device, sitting and standing. In some such methods, the monitoring indicates a reduced movement deficit or a reduced cognitive deficit responsive to administering the antibody.

In some such methods, the synucleinopathy is Parkinson's disease. In some such methods, the synucleinopathy is dementia with Lewy bodies. In some such methods, the synucleinopathy is multiple system atrophy. In some such methods, the synucleinopathy is progressive supra nuclear palsy. In some such methods, the synucleinopathy is REM sleep behavior disorder. In some such methods, the synucleinopathy is Alzheimer's disease with amygdala Lewy bodies. In some such methods, the subject has the disease.

In some such methods, the subject is not receiving symptomatic treatment for Parkinson's disease concomitant with the antibody. In some such methods, the antibody is administered concomitantly with levodopa.

In another aspect, the invention provides a method of treating or effecting prophylaxis of a subject having a Lewy body disease comprising intravenously administering to the subject a dose of 1300-1700 mg of an antibody against alpha-synuclein at intervals of 3-5 weeks, or administering another regime that delivers the antibody to the subject with substantially the same area under the curve.

In some such methods, the dose is 1500 mg. In some such methods, the antibody is administered to a plurality of subjects having Lewy body disease wherein subjects receive either one or two fixed doses. In some such methods, the subject receives a dose of 18-25 mg/kg. In some such methods, the subject receives a dose of 20 mg/kg.

In some such methods, the intervals are 28 days. In some such methods, the subject receives at least six doses of the antibody at the intervals of 3-5 weeks. In some such methods, the subject receives at least 12 doses of the antibody at the intervals of 3-5 weeks. In some such methods, the subject receives at least 18 doses of the antibody at the intervals of 3-5 weeks. In some such methods, the interval is 4 weeks. In some such methods, the subject receives the antibody every 4 weeks for at least 52 weeks.

Some such methods further comprise monitoring the subject for a change in movement, cognitive deficit autonomic dysfunction, gastrointestinal dysfunction, visual hallucination or a psychological symptom.

In some such methods, the monitoring comprises (a) providing a subject with a mobile device programmed to receive and transmit data acquired from sensors internal and/or external to the device relating to movement deficits of a subject having or suspected of having a Lewy body disease, whereafter the subject undergoes a series of movements to reveal movement deficits, if present, and the internal or external sensors of the device acquire data relating to the movements;

(b) collecting data transmitted from the mobile device; and (c) comparing the data acquired from the subjects with control data to assess presence or extent of movement deficits in the subject.

In some such methods, the mobile device is programmed to receive and transmit data from at least two external sensors attached to upper and lower limbs of the subject.

In some such methods, the mobile device acquires data from sensors on the upper and lower limbs of the subject. In some such methods, the mobile device is carried by the subject and acquires data from an internal sensor. In some such methods, the series of movements includes tapping the device, sitting and standing. In some such methods, the monitoring indicates a reduced movement deficit or a reduced cognitive deficit responsive to administering the antibody.

In some such methods, the antibody binds within residues 115-130 of alpha synuclein.

In some such methods, the antibody binds with residues 118-126 of alpha synuclein.

In some such methods, the antibody binds within residues 117-123 of alpha synuclein.

In some such methods, the antibody is NI-202.21D11. In some such methods, the antibody comprises three heavy CDRs designated SEQ ID NOs:139-141 respectively and three light chain CDRs designated SEQ ID NOs: 143-145 respectively. In some such methods, the antibody comprises a heavy chain variable region designated SEQ ID NO:138 and a light chain variable region designated SEQ ID NO:142.

In some such methods, the antibody comprises the three light chain Kabat CDRs of SEQ ID NO:5 and the three heavy chain Kabat CDRs of SEQ ID NO:10. In some such methods, the antibody comprises a heavy chain variable region of any of SEQ ID NOs:8-11 and a light chain variable region of any of SEQ ID NO:3-5, preferably wherein the heavy chain variable region is of SEQ ID NO:10 and a light chain variable region of SEQ ID NO:5.

In some such methods, the antibody is of human IgG1 isotype.

In some such methods, the antibody comprises a heavy chain constant region of SEQ ID NO:35 provided the C-terminal lysine may be absent and a light chain constant region of SEQ ID NO:30. In some such methods, the antibody comprises a heavy chain constant region of SEQ ID NO:35 provided the C-terminal lysine may be absent and a light chain constant region of SEQ ID NO:13.

In some such methods, the antibody comprises three heavy CDRs designated SEQ ID NOs: 146-148 respectively and three light chain CDRs designated SEQ ID NOs: 149-151 respectively. In some such methods, the antibody comprises a heavy chain designated SEQ ID NO:37 and a light chain designated SEQ ID NO:32, wherein the C-terminal lysine of SEQ ID NO:37 may be absent.

In some such methods, the antibody binds within residues 1-20 of alpha-synuclein. In some such methods, the antibody binds with residues 4-15 of alpha-synuclein.

In some such methods, the antibody is NI-202.12F4. In some such methods, the antibody comprises three heavy CDRs designated SEQ ID NOs:131-133 respectively and three light chain CDRs designated SEQ ID NOs: 135-137 respectively. In some such methods, the antibody comprises a heavy chain variable region designated SEQ ID NO:130 and a light chain variable region designated SEQ ID NO:134.

In some such methods, the synucleinopathy is Parkinson's disease. In some such methods, the synucleinopathy is dementia with Lewy bodies. In some such methods, the synucleinopathy is multiple system atrophy. In some such methods, the synucleinopathy is progressive supra nuclear palsy. In some such methods, the synucleinopathy is REM sleep behavior disorder. In some such methods, the synucleinopathy is Alzheimer's disease with amygdala Lewy bodies. In some such methods, the subject has the disease.

In some such methods, the subject is not receiving symptomatic treatment for Parkinson's disease concomitant with the antibody. In some such methods, the antibody is administered concomitantly with levodopa.

Definitions

The term "antibody" includes intact antibodies and binding fragments thereof. Typically, fragments compete with the intact antibody from which they were derived for specific binding to the target. Fragments include separate heavy chains, separate light chains, Fab, Fab', F(ab')2, F(ab)c, Fv, single chain antibodies, and single domain antibodies. The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The basic antibody structural unit is a tetramer of subunits. Each tetramer includes two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. When initially expressed, this variable region is typically linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function. A constant region can include any or all of a CH1 region, hinge region, CH2 region, and CH3 region.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except for bifunctional or bispecific antibodies, the two binding sites are the same. The chains all exhibit the same general structure of relatively conserved framework regions (FR) joined by three hypervariable regions, also called complementarity determining regions (CDRs). The CDRs from the two chains of each pair are aligned by the framework regions, enabling binding to a specific epitope. From N-terminal to C-terminal, both light and heavy chains comprise the regions FR1, CDR1, FR2, CDR2, FR3, CDR3 and FR4. The assignment of amino acids to each region is in accordance with the definitions of Kabat, *Sequences of Proteins of Immunological Interest* (National Institutes of Health, Bethesda, MD, 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chains or between different light chains are assigned the same number.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions (with gaps not counted) multiplied by 100 to convert to percentage.

For purposes of classifying amino acids substitutions as conservative or non-conservative, amino acids are grouped as follows: Group I (hydrophobic sidechains): Norleucine, Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions involve substitutions between amino acids in the same class. Non-conservative substitutions constitute exchanging a member of one of these classes for a member of another.

Antibodies of the invention typically bind to their designated target with an affinity constant of at least $10^6$, $10^7$, $10^8$, $10^9$, or $10^{10}$ M$^{-1}$. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

The term "symptom" refers to subjective evidence of a disease, such as altered gait, as perceived by a subject. A "sign" refers to objective evidence of a disease as observed by a physician.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor. Statistical significance means $p \leq 0.05$.

Unless otherwise apparent from the context, the term "about" encompasses values within the standard deviation of the mean of a stated value or +/−5% of a stated value, whichever is greater.

The term "9E4 antibody" refers to any antibody in which each of the CDRs is substantially that of 9E4, and thus includes murine, chimeric, veneered, and humanized 9E4. References to other antibodies, such as 5C1 and 1H7 have corresponding meanings.

Antibodies of the invention can be administered concomitant with another treatment for the same indication as the antibody, meaning that the other treatment is administered at least once during the period in which the antibody is administered, such period beginning one month before the first dosing and ending one month after the last dosing of the antibody. The other treatment can be administered at recurring intervals during this period, which may or may not be the same as the intervals at which the antibody is administered. The other treatment may be a symptomatic treatment.

A treatment is symptomatic if it only affects one or more symptoms of a disease, not its cause, i.e., its etiology.

The term "mobile device" as used herein refers to any portable device which comprises a sensor and data-recording equipment suitable for obtaining the dataset of activity measurements. Typically, the mobile device comprises a sensor for measuring the activity. This may also require a data processor and storage unit as well as a display for electronically simulating an activity test on the mobile device. Moreover, from the activity of the subject data shall be recorded and compiled to a dataset which is to be evaluated by the method of the present invention either on the mobile device itself or on a second device. Depending on the specific setup envisaged, it may be necessary that the mobile device comprises data transmission equipment in order to transfer the acquired dataset from the mobile device to one or more further devices. Particular well suited as mobile devices according to the present invention are smartphones, smartwatches, wearable sensors, portable multimedia devices or tablet computers. Alternatively, portable sensors with data recording and, optionally, processing equipment may be used. Further, depending on the kind of activity test to be performed, the mobile device shall be adapted to display instructions for the subject regarding the activity to be carried out for the test.

Unless otherwise apparent from the context, reference to a range includes any integer within the range.

A treatment regime refers to a combination of parameters characterizing administration of an immunotherapeutic agent including any or all of dose, frequency of administration, route of administration, and total duration of administration.

BRIEF DESCRIPTION OF THE SEQUENCES

SEQ ID NO:1 is an m9E4VL variable region.
SEQ ID NO:2 is an 63102889Hu9E4VLFr variable region.
SEQ ID NO:3 is an Hu9E4VLv1 variable region.
SEQ ID NO:4 is an Hu9E4VLv2 (No backmutation) variable region.
SEQ ID NO:5 is an Hu9E4VLv3 variable region.
SEQ ID NO:6 is an m9E4VH variable region.
SEQ ID NO:7 is an1791009Hu9E4VHFr variable region.
SEQ ID NO:8 is an Hu9E4VHv1 variable region.
SEQ ID NO:9 is an Hu9E4VHv2 variable region.
SEQ ID NO:10 is an Hu9E4VHv3 variable region.
SEQ ID NO:11 is an Hu9E4VHv4 (no backmutation) variable region.
SEQ ID NO:12 is the amino acid sequence of natural human wildtype alpha-synuclein.
SEQ ID NO:13 is a humanized 9E4 light chain constant region (with R) (common for v1, v2, v3).
SEQ ID NO:14 is a humanized 9E4 light chain constant region (with R) nucleotide sequence (common for v1, v2, v3).
SEQ ID NO:15 is an amino acid sequence of an exemplary human IgG1 constant region.
SEQ ID NO:16 is a nucleic acid sequence encoding an exemplary human IgG1 constant region.
SEQ ID NO:17 is an Hu9E4VLv1 nucleotide sequence variable region.
SEQ ID NO:18 is an Hu9E4VLv2 nucleotide sequence (no backmutation) variable region.

SEQ ID NO:19 is an Hu9E4VLv3 nucleotide sequence variable region.

SEQ ID NO:20 is an Hu9E4VHv1 nucleotide sequence variable region.

SEQ ID NO:21 is an Hu9E4VHv2 nucleotide sequence variable region.

SEQ ID NO:22 is an Hu9E4VHv3 nucleotide sequence variable region.

SEQ ID NO:23 is an Hu9E4VHv4 nucleotide sequence (no backmutation) variable region.

SEQ ID NO:24 is an Hu9E4VL signal peptide (common for v1, v2, v3).

SEQ ID NO:25 is an Hu9E4VL signal peptide nucleotide sequence (common for v1, v2, v3).

SEQ ID NO:26 is an Hu9E4VH signal peptide (common for v1, v2, v3).

SEQ ID NO:27 is an Hu9E4VH signal peptide nucleotide sequence (common for v1, v2, v3, v4).

SEQ ID NO:28 is an Hu9E4VL alternative.

SEQ ID NO:29 is an Hu9E4VH alternative.

SEQ ID NO:30 is an amino acid sequence of an exemplary human kappa light chain constant region.

SEQ ID NO:31 is a humanized 9E4 light chain constant region (without R) nucleotide [0096] sequence (common for v1, v2, v3).

SEQ ID NO:32 is a humanized 9E4 light chain version 3 (variable region+constant region with Arginine).

SEQ ID NO:33 is a humanized 9E4 light chain version 3 (variable region+constant region without Arginine).

SEQ ID NO:34 is a humanized 9E4 heavy chain version 3 (variable region+constant region).

SEQ ID NO:35 is a humanized 9E4 heavy chain constant region (G1m3 allotype; BIP version).

SEQ ID NO:36 is a humanized 9E4 heavy chain version 3 (variable region+constant region).

SEQ ID NO:37 is a humanized 9E4 heavy chain version 3 (variable region+alternative constant region G1m3 allotype).

SEQ ID NO:38 is an m5C1 antibody mature heavy chain variable region nucleotide sequence.

SEQ ID NO:39 is an m5C1 antibody heavy chain variable region amino acid sequence.

SEQ ID NO:40 is an m5C1 antibody heavy chain signal peptide nucleotide sequence.

SEQ ID NO:41 is an m5C1 antibody heavy chain signal peptide amino acid sequence.

SEQ ID NO:42 is an m5C1 antibody mature light chain variable region nucleotide sequence.

SEQ ID NO:43 is an m5C1 antibody light chain variable region amino acid sequence.

SEQ ID NO:44 is an m5C1 antibody light chain signal peptide nucleotide sequence.

SEQ ID NO:45 is an m5C1 antibody light chain signal peptide amino acid sequence.

SEQ ID NO:46 is a 5C1 immunogen.

SEQ ID NO:47 is an m5C1 heavy chain CDR1.

SEQ ID NO:48 is an m5C1 heavy chain CDR2.

SEQ ID NO:49 is an m5C1 heavy chain CDR3.

SEQ ID NO:50 is an m5C1 light chain CDR1.

SEQ ID NO:51 is an m5C1 light chain CDR2.

SEQ ID NO:52 is an m5C1 light chain CDR3.

SEQ ID NO:53 is a murine 5C1 heavy chain variable region nucleotide sequence with sequence encoding signal peptide.

SEQ ID NO:54 is a murine 5C1 heavy chain variable region sequence with signal peptide.

SEQ ID NO:55 is a murine 5C1 light chain variable region nucleotide sequence with sequence encoding signal peptide.

SEQ ID NO:56 is a murine 5C1 light chain variable region sequence with signal peptide.

SEQ ID NO:57 is a human VH Acceptor FR (Acc #AAY42876.1).

SEQ ID NO:58 is a humanized 5C1H1.

SEQ ID NO:59 is a humanized 5C1H2.

SEQ ID NO:60 is a humanized 5C1H3.

SEQ ID NO:61 is a humanized 5C1H4.

SEQ ID NO:62 is a humanized 5C1H5.

SEQ ID NO:63 is a nucleic acid sequence encoding humanized 5C1 H1.

SEQ ID NO:64 is a nucleic acid sequence encoding humanized 5C1 H2.

SEQ ID NO:65 is a nucleic acid sequence encoding humanized 5C1H3.

SEQ ID NO:66 is a nucleic acid sequence encoding humanized 5C1 H4.

SEQ ID NO:67 is a nucleic acid sequence encoding humanized 5C1H5.

SEQ ID NO:68 is a human VL Acceptor FR (Acc #CAB51293.1).

SEQ ID NO:69 is a humanized 5C1L1.

SEQ ID NO:70 is a humanized 5C1L2.

SEQ ID NO:71 is a humanized 5C1L3.

SEQ ID NO:72 is a humanized 5C1L4.

SEQ ID NO:73 is a nucleic acid sequence encoding humanized 5C1 L1.

SEQ ID NO:74 is a nucleic acid sequence encoding humanized 5C1 L2.

SEQ ID NO:75 is a nucleic acid sequence encoding humanized 5C1L3.

SEQ ID NO:76 is a nucleic acid sequence encoding humanized 5C1 L4.

SEQ ID NO:77 is a nucleic acid sequence encoding an exemplary human kappa light chain constant region.

SEQ ID NO:78 is a non-amyloid component (NAC) domain of alpha-synuclein as reported by Jensen et al.

SEQ ID NO:79 is a non-amyloid component (NAC) domain of alpha-synuclein as reported by Uéda et al.

SEQ ID NO:80 is an m1H7 antibody heavy chain variable nucleotide sequence.

SEQ ID NO:81 is an m1H7 antibody heavy chain variable amino acid sequence.

SEQ ID NO:82 is an m1H7 antibody light chain variable nucleotide sequence.

SEQ ID NO:83 is an m1H7 antibody light chain variable amino acid sequence.

SEQ ID NO:84 is a mature m1H7 antibody heavy chain variable nucleotide sequence.

SEQ ID NO:85 is a mature m1H7 antibody heavy chain variable amino acid sequence.

SEQ ID NO:86 is a mature m1H7 antibody light chain variable nucleotide sequence.

SEQ ID NO:87 is a mature m1H7 antibody light chain variable amino acid sequence.

SEQ ID NO:88 is an m1H7 antibody heavy chain CDR1 (Kabat definition).

SEQ ID NO:89 is an m1H7 antibody heavy chain CDR2 (Kabat definition).

SEQ ID NO:90 is an m1H7 antibody heavy chain CDR3 (Kabat definition).

SEQ ID NO:91 is an m1H7 antibody light chain CDR1 (Kabat definition).

SEQ ID NO:92 is an m1H7 antibody light chain CDR2 (Kabat definition).

SEQ ID NO:93 is an m1H7 antibody light chain CDR3 (Kabat definition).

SEQ ID NO:94 is an Hu1H7VHv1 nucleotide sequence.

SEQ ID NO:95 is an Hu1H7VHv1 amino acid sequence.

SEQ ID NO:96 is an Hu1H7VHv2 nucleotide sequence.

SEQ ID NO:97 is an Hu1H7VHv2 amino acid sequence.

SEQ ID NO:98 is an Hu1H7VHv3 nucleotide sequence.

SEQ ID NO:99 is an Hu1H7VHv3 amino acid sequence.

SEQ ID NO:100 is an Hu1H7VHv4 nucleotide sequence.

SEQ ID NO:101 is an Hu1H7VHv4 amino acid sequence.

SEQ ID NO:102 is an Hu1H7VHv5 nucleotide sequence.

SEQ ID NO:103 is an Hu1H7VHv5 amino acid sequence.

SEQ ID NO:104 is an Hu1H7VH signal peptide nucleotide sequence.

SEQ ID NO:105 is an Hu1H7VH signal peptide amino acid sequence.

SEQ ID NO:106 is an Hu1H7VH signal peptide nucleotide sequence.

SEQ ID NO:107 is an Hu1H7VH signal peptide amino acid sequence.

SEQ ID NO:108 is an Hu1H7VLv1 nucleotide sequence.

SEQ ID NO:109 is an Hu1H7VLv1 amino acid sequence.

SEQ ID NO:110 is an Hu1H7VLv2 nucleotide sequence.

SEQ ID NO:111 is an Hu1H7VLv2 amino acid sequence.

SEQ ID NO:112 is an Hu1H7VLv3 nucleotide sequence.

SEQ ID NO:113 is an Hu1H7VLv3 amino acid sequence.

SEQ ID NO:114 is an Hu1H7VLv4 nucleotide sequence.

SEQ ID NO:115 is an Hu1H7VLv4 amino acid sequence.

SEQ ID NO:116 is an Hu1H7VL signal peptide nucleotide sequence.

SEQ ID NO:117 is an amino acid sequence of BAC02037 (GI-21670055) human acceptor used for heavy chain framework.

SEQ ID NO:118 is an amino acid sequence of AAY33358 GI-63102905) human acceptor used for light chain framework.

SEQ ID NO:119 is an Hu1H7VH with no backmutation or CDR mutation.

SEQ ID NO:120 is an Hu1H7VL with no backmutation or CDR mutation.

SEQ ID NO:121 is an Hu1H7VH alternative.

SEQ ID NO:122 is an Hu1H7VL alternative.

SEQ ID NO:123 is an Hu1H7VH CDR3 alternative.

SEQ ID NO:124 is a humanized 1H7 light chain version 3 (variable region+constant region with Arginine).

SEQ ID NO:125 is a humanized 1H7 light chain version 3 (variable region+constant region without Arginine).

SEQ ID NO:126 is a humanized 1H7 heavy chain version 3 (variable region+constant region).

SEQ ID NO:127 is a humanized 1H7 heavy chain version 3 (variable region+constant region G1m3 allotype).

SEQ ID NO:128 is a humanized 1H7 heavy chain constant region (IgG2).

SEQ ID NO:129 is a humanized 1H7 heavy chain constant region (G1m1 allotype).

SEQ ID NO:130 is a NI-202.12F4-VHA1b variable heavy chain (VH) sequence.

SEQ ID NO:131 is a NI-202.12F4-VHA1b CDR1 sequence.

SEQ ID NO:132 is a NI-202.12F4-VHA1b CDR2 sequence

SEQ ID NO:133 is a NI-202.12F4-VHA1b CDR3 sequence.

SEQ ID NO:134 is a NI-202.12F4-VLa1 variable light chain (VL) sequence.

SEQ ID NO:135 is a NI-202.12F4-VLa1 CDR1 sequence.

SEQ ID NO:136 is a NI-202.12F4-VLa1 CDR2 sequence.

SEQ ID NO:137 is a NI-202.12F4-VLa1 CDR3 sequence.

SEQ ID NO:138 is a NI-202.21D11-VH sequence.

SEQ ID NO:139 is a NI-202.21D11-VH CDR1 sequence.

SEQ ID NO:140 is a NI-202.21D11-VH CDR2 sequence.

SEQ ID NO:141 is a NI-202.21D11-VH CDR3 sequence.

SEQ ID NO:142 is a NI-202.21D11-VK sequence.

SEQ ID NO:143 is a NI-202.21D11 VK CDR1 sequence.

SEQ ID NO:144 is a NI-202.21D11 VK CDR2 sequence.

SEQ ID NO:145 is a NI-202.21D11 VK CDR3 sequence.

SEQ ID NO:146 is a 9E4 VH CDR1 sequence.

SEQ ID NO:147 is a 9E4 VH CDR2 sequence.

SEQ ID NO:148 is a 9E4 VH CDR3 sequence.

SEQ ID NO:149 is a 9E4 VL CDR1 sequence.

SEQ ID NO:150 is a 9E4 VL CDR2 sequence.

SEQ ID NO:151 is a 9E4 VL CDR3 sequence.

DETAILED DESCRIPTION

I. GENERAL

The invention provides dosing regimes for immunotherapy of synucleinopathies. Subjects receive an antibody against alpha-synuclein at a dose of 3000-5000 mg or 1300-1700 mg intravenously every 3-5 weeks. Such doses can be preceded by one or more lower loading doses.

II. TARGET MOLECULE

Natural human wild type alpha-synuclein is a peptide of 140 amino acids having the following amino acid sequence:

```
                                        (SEQ ID NO: 12)
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

(Ueda et al., Proc. Natl. Acad. Sci. USA (1993) 90:11282-6); GenBank accession number: P37840. The protein has three recognized domains: an-N-terminal KTKE repeat domain covering amino acids 1-61; a NAC (Non-amyloid component) domain running from about amino acids 60-95; and a C-terminal acidic domain running from about amino acid 98 to 140.

Unless otherwise apparent from the context, reference to alpha-synuclein or its fragments includes the natural human wildtype amino acid sequences indicated above, and human allelic variants thereof, particularly those associated with Lewy body disease (e.g., variants E46K, A30P and A53T, with the first letter indicating the amino acid in SEQ ID NO:12, the number indicating the codon position in SEQ ID NO:12, and the second letter indicating the amino acid in the allelic variant). Such variants can optionally be present individually or in any combination in any of the aspects of the invention described below.

III. SYNUCLEINOPATHIES

Synucleinopathies are characterized by excessive accumulation of alpha-synuclein, which may or may not involve the formation of Lewy bodies (LBs). Lewy Body Diseases (LBD), for example, are characterized by degeneration of the dopaminergic system, motor alterations, cognitive impairment, and formation of Lewy bodies. (McKeith et al., Neurology (1996) 47:1113-24). Lewy Bodies are spherical protein deposits found in nerve cells. Their presence in the brain disrupts the brain's normal function interrupting the action of chemical messengers including acetylcholine and dopamine. Synucleinopathies include Parkinson's disease (including idiopathic Parkinson's disease), Dementia with Lewy Bodies (DLB) (also known as Diffuse Lewy Body Disease (DLBD)), Lewy Body variant of Alzheimer's disease (LBV), Combined Alzheimer's and Parkinson disease, progressive supra nuclear palsy (PSP), and multiple system atrophy (MSA; e.g., Olivopontocerebellar Atrophy, Striatonigral Degeneration, and Shy-Drager Syndrome). DLB shares symptoms of both Alzheimer's and Parkinson's disease. DLB differs from Parkinson's disease mainly in the location of Lewy Bodies. In DLB Lewy Bodies form mainly in the cortex. In Parkinson's disease, they form mainly in the substantia nigra. Other synucleinopathies include Pure Autonomic Failure, Lewy Body dysphagia, Incidental LBD, and Inherited LBD (e.g., mutations of the alpha-synuclein gene, PARK3 and PARK4).

IV. IMMUNOTHERAPY AGENTS

Passive immunotherapy involves treatment with an antibody specifically binding to alpha-synuclein.

1. ANTIBODIES

A. Binding Specificity and Functional Properties

The present methods can include antibodies specifically binding to an epitope within residues 1-15, 4-15, 1-20, 91-99, 115-130, 117-123 or 118-126 of human alpha-synuclein. Antibodies can be monoclonal or polyclonal. A polyclonal serum can be specific to an epitope or range of amino acids within alpha-synuclein in that it lacks antibodies binding outside the epitope or range. Antibodies can be non-human, chimeric, veneered, humanized, or human among other possibilities.

Some antibodies are bispecific, one arm of which is an antibody against alpha-synuclein and the other arm of which is an antibody that binds to a receptor expressed on the blood brain barrier, such as an insulin receptor, an insulin-like growth factor (IGF) receptor, a leptin receptor, or a lipoprotein receptor, or preferably a transferrin receptor (Friden et al., PNAS 88:4771-4775, 1991; Friden et al., Science 259: 373-377, 1993). Such a bispecific antibody can be transferred cross the blood brain barrier by receptor-mediated transcytosis. Brain uptake of the bispecific antibody can be further enhanced by engineering the bispecific antibody to reduce its affinity to the blood brain barrier receptor. Reduced affinity for the receptor resulted in a broader distribution in the brain (see, e.g., Atwal. et al. *Sci. Trans. Med.* 3, 84ra43, 2011; Yu et al. *Sci. Trans. Med.* 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

Another exemplary antibody is mAb 9E4, which binds to an epitope within residues 118-126 of human alpha-synuclein. The cell line designated JH17.9E4.3.37114.2 producing the antibody 9E4 has the ATCC accession number PTA-8221 having been deposited under the provisions of the Budapest Treaty with the American Type Culture Collection (ATCC, P.O. Box 1549, Manassas, Va. 20108) on Feb. 26, 2007. The murine light and heavy chain variable sequences are SEQ ID NO:1 and SEQ ID NO:6, respectively. Murine mAb 9E4 comprises a VH-CDR1 of SEQ ID NO:146, a VH-CDR2 of SEQ ID NO:147, a VH-CDR3 of SEQ ID NO:148, a VL-CDR1 of SEQ ID NO: 149, a VL-CDR2 of SEQ ID NO:150, and a VL-CDR3 of SEQ ID NO: 151.

Another exemplary antibody is mAb 5C1. The murine light and heavy chain variable sequences are SEQ ID NO:43 and SEQ ID NO:39, respectively.

Another exemplary antibody is mAb 1H7. The cell line designated JH17.1H7.4.24.34 producing the antibody 1H7 has the ATCC accession number PTA-8220 having been deposited under the provisions of the Budapest Treaty with the American Type Culture Collection (ATCC, P.O. Box 1549, Manassas, Va. 20108) on Feb. 26, 2007. The murine light and heavy chain variable sequences are SEQ ID NO:87 and SEQ ID NO:85, respectively.

Such antibodies are described in WO 06/020581 and U.S. application Ser. Nos. 61/591,835, 61/711,207, 13/750,983, 61/711,204, 61/719,281, 61/840,432, 61/872,366, 14/049, 169, 61/553,131, 61/711,204, 61/843,011, and 13/662,261, all of which are incorporated herein by reference for all purposes.

Another exemplary antibody is NI-202.12F4, which is a human antibody reported to bind to an epitope within residues 4-15 of alpha-synuclein with residue 10 being a major contributor to the epitope (see U.S. Pat. No. 8,940, 276; WO2012177972, U.S. Pat. No. 9,580,493). NI-202.12F4 comprises a variable heavy chain (VHA1b) sequence of SEQ ID NO:130 and a variable light chain (VLa1) sequence of SEQ ID NO:134. NI-202.12F4 comprises a VHA1b-CDR1 of SEQ ID NO:131, a VHA1b-CDR2 of SEQ ID NO:132, a VHA1b-CDR3 sequence of SEQ ID NO:133 (Ala-His), a VLa1-CDR1 sequence of SEQ ID NO:135, a VLa1-CDR2 sequence of SEQ ID NO: 136, and VLa1-CDR3 sequence of SEQ ID NO:137. Another exemplary antibody is NI-202.21D11, which has been reported to bind to an epitope within residues 117-123 of alpha-synuclein with residues 121 and 122 contributing most to the epitope (see U.S. Pat. No. 9,580,493). NI-202.21D11 comprises a variable heavy chain (VH) sequence of SEQ ID NO:138 and a variable light chain (VK) sequence of SEQ ID NO:142. NI-202.21D11 comprises a VH-CDR1 of SEQ ID NO:139, a VH-CDR2 of SEQ ID NO:140, a VH-CDR3 sequence of SEQ ID NO:141, a VK-CDR1 sequence of SEQ ID NO:143, a VK-CDR2 sequence of SEQ ID NO: 144, and VK-CDR3 sequence of SEQ ID NO:145.

B. Humanized Antibodies

A humanized antibody is a genetically engineered antibody in which the CDRs from a non-human "donor" antibody are grafted into human "acceptor" antibody sequences (see, e.g., Queen et al., U.S. Pat. Nos. 5,530,101 and 5,585,089; Winter et al., U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody variable region sequence, a composite of such sequences, a consensus sequence of human antibody sequences (e.g., light and heavy chain variable region consensus sequences of Kabat, 1991, supra), or a germline variable region sequence. Thus, a humanized antibody of the invention includes antibodies having three light chain and three heavy chain CDRs as defined by Kabat entirely or substantially from a murine antibody, such as 9E4, 5C1 or 1H7 (donor antibody) and mature variable region framework sequences and constant regions, if present, entirely or substantially from human antibody sequences. Likewise a humanized heavy chain includes heavy chains having three heavy chain CDRs as defined by Kabat from the heavy chain of the donor antibody, and a mature heavy chain variable sequence and heavy chain constant region sequence, if present, entirely or substantially from human antibody heavy chain sequences. Likewise a humanized light chain includes light chains having three light chain CDRs as defined by Kabat from the light chain of the donor antibody, and a mature light chain variable sequence and light chain constant region sequence, if present, entirely or substantially from human antibody light chain sequences. The mature variable region framework sequences of an antibody chain or the constant region sequence of an antibody chain are substantially from a human mature variable region framework sequence or human constant region sequence, respectively, when at least 85%, 90%, 95%, 96%, 97%, 98%, 99% or 100% of corresponding residues defined by Kabat are identical. A CDR is substantially from a corresponding donor CDR if showing at least 85% identity thereto, except in the case of CDRH2 wherein at least 65% identify is required.

Certain amino acids from the human mature variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine mature variable region framework residue and a selected human mature variable region framework residue, the human framework amino acid can be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g. is within about 6 Å of a CDR region)

(4) mediates interaction between the heavy and light chains.

Exemplary humanized forms of the mouse 9E4 antibody including three exemplified humanized light chain mature variable regions (Hu9E4VLv1-v3; SEQ ID NOs:3-5) and four exemplified humanized heavy chain mature variable regions (Hu9E4VHv1-v4; SEQ ID NOs:8-11).

The exemplary light and heavy chain mature variable regions can be paired in any combination. An exemplary combination is Hu9E4VLv3 (SEQ ID NO:5) and Hu9E4VHv3 (SEQ ID NO:10). An exemplary heavy chain constant region is SEQ ID NO:35, with or without the C-terminal lysine. This constant region can be linked to any of the heavy chain variable regions. An exemplary light chain constant region is SEQ ID NO:30. This constant region can be linked to any of the light chain variable regions. An exemplary full length heavy chain has the amino acid sequence of SEQ ID NO:37, with or without the C-terminal lysine. An exemplary full length light chain has the amino acid sequence of SEQ ID NO:32. An exemplary combination is an antibody comprising SEQ ID NO:37 (with or without the C-terminal lysine) and SEQ ID NO:32. The nucleic acids encoding the various heavy and light chains just described are provided in SEQ ID NOs:17-23. An exemplified humanized antibody has heavy and light chains characterized by SEQ ID NOs: 37 (with or without the C-terminal lysine) and 32.

Exemplary humanized forms of the mouse 5C1 antibody include four exemplified humanized light chain mature variable regions (5C1L1-L4; SEQ ID NOs:69-72, and five exemplified humanized heavy chain mature variable regions (5C1H1-H4; SEQ ID NOs:58-62). The exemplary light and heavy chain mature variable regions can be paired in any combination. An exemplary heavy chain constant region is SEQ ID NO:35, with or without the C-terminal lysine. This constant region can be linked to any of the heavy chain variable regions. An exemplary light chain constant region is SEQ ID NO:30. This constant region can be linked to any of the light chain variable regions. The nucleic acids encoding the various heavy and light chains just described are provided in SEQ ID NOs:73-76 and 63-67.

Exemplary humanized forms of the mouse 1H7 antibody include four exemplified humanized light chain mature variable regions (Hu1H7VLv1-v4; SEQ ID NOs:109, 111, 113, and 115, respectively and five exemplified humanized heavy chain mature variable regions (Hu1H7VHv1-v5; SEQ ID NOs:95, 97, 99, 101, and 103, respectively). The exemplary light and heavy chain mature variable regions can be paired in any combination. An exemplary combination is Hu1H7VHv3 (SEQ ID NO:99) and Hu1H7VLv3 (SEQ ID NO:113). An exemplary heavy chain constant region is SEQ ID NO:35, with or without the C-terminal lysine. This constant region can be linked to any of the heavy chain variable regions. An exemplary light chain constant region is SEQ ID NO:30. This constant region can be linked to any of the light chain variable regions. An exemplified full length heavy chain has the amino acid sequence of SEQ ID NO:127 (with the G1m3). An exemplary full length light chain has the amino acid sequence of SEQ ID NO:125 (without Arginine). An exemplary combination is an antibody comprising SEQ ID NO:127 and SEQ ID NO:125. The nucleic acids encoding the various heavy and light chains just described are provided in SEQ ID NOs 108, 110, 112, 114, 94, 96, 98, 100, 102.

Such humanized antibodies are described in WO 06/020581 and U.S. Ser. Nos. 13/750,983, 14/049,169, 13/662,261, and 61/843,011.

In these or other antibodies described herein, one or more terminal residues can be cleaved in the course of posttranslational processing, particularly for terminal lysines of heavy chain constant regions.

C. Chimeric and Veneered Antibodies

The invention further provides chimeric and veneered forms of non-human antibodies, particularly 9E4, 5C1 or1H7.

A chimeric antibody is an antibody in which the mature variable regions of light and heavy chains of a non-human antibody (e.g., a mouse) are combined with light and heavy chain constant regions from an antibody of a different species. Typically, the light and heavy chain constant regions are of human origin, but the constant regions can originate from a different non-human species, such as a rat, as needed (e.g., to facilitate testing of the non-human antibody in an appropriate animal model). Such antibodies substantially or entirely retain the binding specificity of the non-human (e.g., mouse) antibody supplying the variable regions, and are about two-thirds human (or different non-human species) sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of 9E4 are included in the invention.

D. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotopes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. An exemplary human light chain kappa constant region has the amino acid sequence of SEQ ID NO:13. Some such light chain kappa constant regions can be encoded by a nucleic acid sequence. The N-terminal arginine of SEQ ID NO:13 can be omitted, in which case light chain kappa constant region has the amino acid sequence of SEQ ID NO:30. Some such light chain kappa constant regions can be encoded by a nucleic acid sequence. An exemplary human IgG1 heavy chain constant region has the amino acid sequence of SEQ ID NO:15 (with or without the C-terminal lysine) or the heavy chain constant region component of SEQ ID NO:37 (with or without the C-terminal lysine). Some such heavy chain constant regions can be encoded by a nucleic acid sequence. Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 allotype and has the amino acid sequence encoding a constant region of SEQ ID NO:37. Yet another heavy chain constant region has the amino acid sequence encoding a constant region of SEQ ID NO:37 except that it lacks the C-terminal lysine.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for $Fc\gamma$ receptors, particularly $Fc\gamma RI$ receptor (see, e.g., U.S. Pat. No. 6,624,821). Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624, 821).

E. Expression of Recombinant Antibodies

Antibodies can be produced by recombinant expression. Nucleic acids encoding the antibodies can be codon-optimized for expression in the desired cell-type (e.g., CHO or Sp2/0). Recombinant nucleic acid constructs typically include an expression control sequence operably linked to the coding sequences of antibody chains, including naturally-associated or heterologous promoter regions. The expression control sequences can be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase, to allow amplification of copy number of the nucleic acids encoding the antibody chains.

E. coli is a prokaryotic host particularly useful for expressing antibodies, particularly antibody fragments. Microbes, such as yeast are also useful for expression. Saccharomyces is an exemplary yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. It can be advantageous to use nonhuman cells. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Suitable expression control sequences are promoters derived from endogenous genes, cytomegalovirus, SV40, adenovirus, bovine papillomavirus, and the like. See Co et al., *J. Immunol.* 148:1149 (1992).

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be advantageous. Antibodies produced by single cell clones can also be tested for turbidity, filtration properties, PAGE, IEF, UV scan, HP-SEC, carbohydrate-oligosaccharide mapping, mass spectrometery, and binding assay, such as ELISA or Biacore. A selected clone can then be banked in multiple vials and stored frozen for subsequent use.

Once expressed, antibodies can be purified according to standard procedures of the art, including protein A capture, column chromatography (e.g., hydrophobic interaction or ion exchange), low-pH for viral inactivation and the like (see generally, Scopes, *Protein Purification* (Springer-Verlag, NY, 1982)).

Methodology for commercial production of antibodies including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 6,114,148, 6,063,598, 7,569,339, WO2004/050884, WO2008/012142, WO2008/012142, WO2005/019442, WO2008/107388, and WO2009/027471, and U.S. Pat. No. 5,888,809).

V. FORMULATIONS

Formulations (also known as pharmaceutical compositions) of the invention comprise an antibody (e.g., a chimeric, veneered or humanized version of murine 9E4 (ATCC Accession Number PTA-8221)) or antigen binding fragment thereof, a buffer, one or more sugars and/or polyols and a surfactant, and have a pH within the range from about 5 to about 7.5. The formulations can be prepared for storage in liquid form or in lyophilized form. When stored in lyophilized form, the formulations can be reconstituted with a liquid (e.g., sterile water) to the concentrations and properties described herein. When a lyophilized composition is said to be reconstitutable by adding water to generate a formulation of specified component concentrations and pH, it is meant that the lyophilized formulation can be so reconstituted simply by addition of water (i.e., without supplying additional amounts of components or adding acid or base to change the pH). The concentrations and properties of a prelyophilized liquid formulation can also be in accordance with those described below if the lyophilized formulation is reconstituted to the same volume as the formulation prelyophilization. If the volume is different, then concentrations of formulations should be adjusted proportionally. For example, if the reconstituted volume is half the prelyophilization volume, then the concentrations of components in the prelyophilization formulation should be half the concentrations in the reconstituted formulation.

Some formulations include a bulking agent, which may or may not be the same as a sugar/polyol component. Typically, the formulations are sterile, for example, as accomplished by sterile filtration using a 0.2 μm or a 0.22 μm filter. Some formulations have a bioburden of ≤about 3 CFU/30 mL. Some formulations contain ≤about 0.1 EU/mg of bacterial endotoxins. The formulations of the invention are also generally stable by low to undetectable levels of fragmentation and/or aggregation as further defined below on freezing and thawing. Still other formulations are stable following reconstitution of a lyophilized cake for at least three months at 40 degrees Celsius. In some formulations, less than about 10% of the antibody is present as an aggregate in the formulation. In some formulations, less than or equal to about 5% of the antibody is present as an aggregate in the formulation.

In some formulations, the antibody is present at a concentration within the range from about 5 mg/mL to about 100 mg/mL. In some formulations, the antibody is present at a concentration within the range from about 5 mg/mL to about 50 mg/mL. In some formulations, the antibody is present at a concentration within the range from about 25 mg/mL to about 50 mg/mL. For example, the antibody may be present at a concentration of about 35-45 mg/ml or about 40 mg/mL. The antibody may be present in a sterile liquid dosage form of about 50 mg/vial to about 500 mg/vial, or greater. The antibody may be present in a lyophilized dosage form of about 40 mg/vial to about 500 mg/vial. For example, the antibody may be present in a sterile liquid or lyophilized dosage form of about 250-350 mg/vial or about 200 mg/vial.

Antibodies used in the disclosed formulations can be coupled with a therapeutic moiety, such as a cytotoxic agent, a radiotherapeutic agent, an immunomodulator, a second antibody (e.g., to form an antibody heteroconjugate), or any other biologically active agent that facilitates or enhances the activity of the formulated antibody. However, antibodies are usually used in naked form (i.e., not conjugated to any of these moieties).

The formulated antibody can be any of the antibodies described above including any of the chimeric, veneered or humanized versions of antibody 9E4 described above.

Buffers are used in the disclosed formulations to achieve a suitable pH for the antibody, such as, for example, histidine, succinate, and citrate buffers. Some formulations have a pH within the range from about 5.5 to about 7, for example, a pH of 5.5, 5.6, 5.7, 5.8, 5.9, 6.0, 6.1, 6.2, 6.3, 6.4, 6.5, 6.6, 6.7, 6.8, 6.9, or 7.0. Some formulations have a pH of between about 5.5 to about 6.5. Some formulations have a pH of about 6.0 and other formulations have a pH of about 6.5. In some formulations, citrate buffer or succinate buffer is present at a concentration within the range from about 10 mM to about 30 mM, for example, at a concentration of about 15-25 mM or about 20 mM. Some citrate buffers comprise sodium citrate dehydrate and citric acid monohydrate at a concentration within the range from about 15 mM to about 20 mM and a range from about 2 mM to about 6 mM, respectively.

Suitable sugars and/or polyols for the formulations include trehalose, sucrose, mannitol, or a combination thereof. Sugars/polyols serves as bulking agents, lyoprotecting agent, and/or tonicity adjusting agents. For example, some formulations include trehalose present at a concentration within the range from about 220 mM to about 260 mM, sucrose present at a concentration within the range from about 220 mM to about 260 mM, or a mixture of sucrose present at a concentration within the range from about 20 mM to about 40 mM and mannitol present at a concentration within the range from about 200 mM to about 220 mM. Some formulations include trehalose present at a concentration of about 230 mM or 240 mM. Other formulations include sucrose present at a concentration of about 230 mM or 240 mM. Other formulations include a mixture of sucrose present at a concentration of about 50 mM and mannitol present at a concentration of about 200 mM. Another formulation includes a mixture of sucrose present at a concentration of about 28 mM and mannitol present at a concentration of about 212 mM. Some such formulations are characterized by an osmolality in the range of about 250-400, 300-400, or 300-350 mOsm/kg, such as, for example, 335 mOsm/kg.

Formulations can contain a surfactant to reduce antibody aggregation and absorption to surfaces. Suitable surfactants include polysorbate 20 (PS20) present at a concentration within the range from about 0.005% to about 0.05% by weight. PS20 protects against marked increases in aggregation or turbidity that would otherwise occur in formulations of 9E4 antibodies. The polysorbate 20 may be present at a concentration within the range from about 0.01% to about 0.05%. For example, the concentration can be 0.005%, 0.01%, 0.015%, 0.02%, 0.025%, 0.03%, 0.035%, 0.04%, 0.045%, or 0.05%. Alternatively, in some formulations, polysorbate 20 is present at a concentration within the range of about from about 0.05 g/L, 0.1 g/L, 0.15 g/L, 0.2 g/L, 0.25 g/L, 0.3 g/L, 0.35 g/L, 0.4 g/L, 0.45 g/L, or 0.5 g/L. Some formulations include polysorbate 20 at a concentration of 0.2 g/L (i.e., 0.163 mmol/L).

An exemplary formulation (liquid, prelyophilization or reconstituted after lyophilization) is characterized by a pH within the range from about 5.5 to about 7 and includes: (a) a chimeric, veneered, or humanized version of antibody 9E4, or a fragment thereof that specifically competes for binding to antigen with 9E4 at a concentration within the range from about 10 mg/ml to about 50 mg/ml; (b) a citrate buffer or succinate buffer present at a concentration within the range from about 10 mM to about 30 mM; (c) one or more sugars and polyols ("sugar/polyol") selected from trehalose present at a concentration within the range from about 220 mM to about 260 mM, sucrose present at a concentration within the range from about 220 mM to about 260 mM, and a mixture of sucrose present at a concentration within the range from about 20 mM to about 40 mM and mannitol present at a concentration within the range from about 200 mM to about 220 mM; and (d) polysorbate 20 present at a concentration within the range from about 0.005% to about 0.05% by weight. For example, the formulation can include: (a) an antibody comprising a light chain having the amino acid sequence set forth as SEQ ID NO: 32 and a heavy chain comprising an amino acid sequence set forth as SEQ ID NO: 37, with or without the C-terminal lysine, and which is present at a concentration of about 40 mg/mL; (b) a citrate buffer at a concentration of about 20 mM; (c) trehalose at a concentration of about 230 mM; (d) polysorbate 20 at a concentration of about 0.02%; and a pH of about 6.0.

Some lyophilized formulations include: (a) a humanized version of antibody 9E4 or an antigen binding fragment thereof; (b) citrate; (c) trehalose; and polysorbate 20. The lyophilized formulation can include about 200 mg of the antibody. Some lyophilized formulations are capable of being reconstituted with sterile water. Some lyophilized formulations include 100-300 or 150-250 mg 9E4 antibody, 15-35 or 20-25 mg sodium citrate dehydrate, 1.65-2.75 or 2-2.3 mg citric acid monohydrate, 360-500 or 400-470 mg trehalose dehydrate, and 0.5 to 1.5 mg or 0.75 to 1.25 mg polysorbate 20. An exemplary lyophilized formulation includes 200 mg of a 9E4 antibody (e.g., humanized 9E4 antibody), 25 mg of sodium citrate dehydrate, 2.15 mg citric acid monohydrate, 435 mg trehalose dehydrate, and 1 mg polysorbate 20. Another exemplary lyophilized formulation includes 200 mg of a 9E4 antibody (e.g., humanized 9E4 antibody), 25 mg of sodium citrate dehydrate, 3.15 mg citric acid monohydrate, 435 mg trehalose dehydrate, and 1 mg polysorbate 20. Such formulations can be reconstituted to a volume of about 5 ml. Other lyophilized formulations include the same components in the same proportions as any disclosed in this paragraph but in different amounts (e.g., 400 mg antibody, 50 mg sodium citrate, 4.3 mg citric acid monohydrate, 870 mg Trehalose dehydrate, and 2 mg polysorbate 20).

Lyophilized formulations can be reconstituted to an antibody concentration of about 30-50 or 35-45 mg/mL, such as about 40 mg/mL; (b) a citrate buffer present at a concentration of about 10-30 or 15-25 mM, preferably about 20 mM; (c) trehalose present at a concentration of about 160-330 or 200-260 mM, such as about 230 mM; (d) polysorbate 20 present at a concentration of about 0.1-0.3 or 0.15 to 0.25 g/L, such as about 0.2 g/L; and (e) a pH of about 5.5-6.5, such as about 6.0.

Liquid or reconstituted lyophilized formulations can be substantially isotonic, implying an osmolality of about 250-350 mOsm/kg water. Some formulations have an osmolality of about 335 mOsm/kg. Some formulations have an osmolality of 270-300 mOsm/kg. Liquid or reconstituted lyophilized formulations can also be hypertonic >350 mOsm/kg water or hypotonic (<250 mOsm/kg water).

Any of the formulations described can be made without pharmaceutical excipients, carriers or the like, other than those described as being components herein. Such a formulation can be described as consisting of the recited components, or consisting essentially of the recited components if insignificant amounts of other components not affecting the properties of the formulation are present. Formulations can be made under good manufacturing practices (GMP) approved or approvable by the FDA for preparation of drugs for administration to humans.

VI. DIAGNOSTIC CRITERIA FOR SYNUCLEINOPATHIES

The present methods are in general performed on subjects diagnosed with a Lewy body disease by a qualified health practitioner or are at elevated risk thereof compared with the general population as evidenced by genetic or biochemical markers, family history or prodromal symptoms of the disease. Such individuals include any who have received a prior prescription for treatment or prophylaxis of a Lewy body disease. Diagnosis of the synucleinopathy can be based on art-recognized criteria for possible or probable Lewy body disease, such as those of DSM-V or DSM IV-TR, the Lewy Body dementia association, the Parkinson's disease society and the like. However, diagnosis can also be based on presence of any signs or symptoms of Lewy body disease that lead a treating physician to conclude that a subject probably has a Lewy body disease. Exemplary criteria for diagnosing possible or probable PD are shown below.

Group A: resting tremor, bradykinesia, rigidity and asymmetric onset

Group B features: suggestive of alternative diagnoses

Prominent postural instability in the first 3 years after symptom onset

Freezing phenomena in the first 3 years

Hallucinations unrelated to medications in the first 3 years

Dementia preceding motor symptoms or in the first year

Supranuclear gaze palsy (other than restriction of upward gaze) or slowing of vertical saccades Severe symptomatic dysautonomia unrelated to medications Documentation of a condition known to produce parkinsonism and plausibly connected to the subject's symptoms (such as suitably located focal brain lesions or neuroleptic use within the past 6 months).

Criteria for possible diagnosis of Parkinson disease:

At least 2 of the 4 features in Group A are present; at least 1 of these is tremor or bradykinesia and either none of the features in group B is present or symptoms have been present for less than 3 years and none of the features in group B is present to date; and either substantial and sustained response to levodopa or a dopamine agonist has been documented, or the subject has not had an adequate trial of levodopa or dopamine agonist.

Criteria for probable diagnosis of Parkinson disease:

At least 3 or the 4 features in Group A are present, and none of the features in Group B is present and substantial and sustained response to levodopa or a dopamine agonist has been documented.

Exemplary criteria for diagnosis of Lewy Body dementia are:

The presence of dementia

At least two of three core features:

fluctuating attention and concentration, recurrent well-formed visual hallucinations, and spontaneous parkinsonian motor signs.

Suggestive clinical features include:

Rapid eye movement (REM) sleep behavior disorder

Severe neuroleptic sensitivity

Low dopamine transporter uptake in basal ganglia demonstrated by SPECT or PET imaging In the absence of two core features, the diagnosis of probable DLB can also be made if dementia plus at least one suggestive feature is present with one core feature.

Possible DLB can be diagnosed with the presence of dementia plus one core or suggestive feature.

Early warning signs of Lewy Body disease include for example, EEG slowing, neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia) and miscellaneous other signs and symptoms (fatigue, diplopia, blurred vision, seborrhea, weight loss/gain). Genetic markers of risk toward PD include mutations in the alpha-synuclein or Parkin, UCHLI, and CYP2D6 genes; particularly mutations at positions 30 and 53 of the alpha-synuclein gene. None of these genetic markers or early warning sign is itself diagnostic of a Lewy body disease but they can individually or in combination contribute to a diagnosis of a Lewy body disease.

VII. THERAPEUTIC REGIMES

In therapeutic applications, an antibody is administered to a subject diagnosed with a synucleinopathy in a regime (dose, frequency and route of administration) known or suspected to be effective to ameliorate or at least inhibit further deterioration of at least one sign or symptom of the disease. In prophylactic applications, an antibody is administered to a subject at increased risk of a synucleinopathy but not yet having sufficient symptoms to be diagnosed with the disease in a regime known or suspected to be effective to inhibit or delay onset of at least one sign or symptom of the disease.

A regime is considered therapeutically or prophylactically effective if a more favorable outcome is demonstrated in treated subjects versus control subjects in a controlled animal model or clinical trial (e.g., a phase II, phase II/III or phase III trial) at the $p<0.2$, 0.1, 0.05 or 0.01 or even 0.001 level. However, due to variations in genetics, subject characteristic and environment and disease subtype between individual subjects, a regime that is effective in one subject may not be effective in another subject or may be effective to different extents.

An exemplary dosage range for antibodies is from 3000 to 5000 mg of an antibody against alpha-synuclein administered intravenously at intervals of 3-5 weeks, such as every 4 weeks. In some subjects, the dosage is 3500-4500 mg every 3-5 weeks, such as every 4 weeks. Subjects can receive the same or different dosages as each other (e.g., depending on weight of the subject). In some methods, a subject receives one of two fixed dosages. For example, subjects with a weight less than 65 kg can receive 3500 mg and subjects with a weight greater or equal to 65 kg can receive 4500 mg. In some methods, the dosage range for at least some subjects lies within a range of 45-75 mg/kg, for example, 50-70 mg/kg, 45 mg/kg, 60 mg/kg or 65 mg/kg. Dosages are usually administered on multiple occasions with an interval of 3-5 weeks, such as every 28 days or four weeks, or every calendar month. Subjects can receive at least 6, 9, 12 or 18 dosages at such intervals, or can be dosed while symptoms of the conditions persist or for the remaining life of the subject. In some regimes, an initial loading dose of 2000 mg is administered followed by dosing within a range of greater or equal to 2000 mg but less than the intended target dose until the intended target dose is reached. For example, a subject can receive an initial loading dose of 2000 mg, followed by an up-titration to a 3500 mg dose or a 4500 mg dose. The up-titration can occur in a single subsequent dose or in gradual increases over several doses until a target dose or dose within a target range is reached. For example, a subject can receive an initial dose of 2000 mg followed by subsequent doses of 3500 mg. Alternatively a subject can receive an initial dose of 2000 mg followed by one or more subsequent doses at greater or equal to 2000 mg but less than 3500 mg, and subsequent doses at 3500 mg. Likewise a subject can receive an initial dose of 2000 mg followed by subsequent doses of 4500 mg. Alternatively, a subject can receive an initial dose of 2000 mg followed by subsequent doses at greater or equal to 2000 mg but less than 4500 mg and subsequent doses at 4500 mg. In some regimes a subject receives a dose of 3000-5000 mg antibody intravenously every four weeks for at least 52 weeks. In subjects receiving multi-dose regimes with the dose within a specified range, such as 3500-5000 mg, the subject can receive the same or different dose within the specified range on each dosing. In some regimes, a subject receives the same dose within a specified range at each dosing.

In another exemplary regime, a dose of 1300-1700 mg antibody is administered intravenously to a subject at intervals of 3-5 weeks. An exemplary dose is 1500 mg. Subjects can received a single fixed dose or two or more different dosages within this range, based on e.g., subject weight. Some subjects dosed within this range receive 18-25 mg/kg of antibody, for example, 20 mg/kg. As in other methods, the intervals can be 3-5 weeks, such as every 4 weeks or every calendar month. Subjects can receive at least 6, at least 9, at least 12, or at least 18 dosages, or can be dosed at such intervals while symptoms remain or for the remaining life of a subject.

For any of the above described treatment regimes, an area under the curve can be calculated to indicate the amount of antibody delivered with time. Alternative treatment regimes can be devised (e.g., with a different route of administration, frequency or dose) to deliver substantially the same area under the curve (e.g., within 25, 20 or 15%). Preferably such an alternative treatment regime does not substantially exceed the Cmax of the specified regime (e.g., by no more than 25, 20 or 15%). Other routes of administration include topical, oral, subcutaneous, intraarterial, intracranial, intrathecal, intraperitoneal, intranasal or intramuscular.

Any of the treatment regimes can be accompanied by monitoring a subject receiving treatment for changes in movement and/or cognitive deficits. Preferably such monitoring includes at least one assessment before and after commencing treatment. Preferably the monitoring indicates reduced movement and/or cognitive deficits responsive to treatment, that is relative to before beginning treatment or at least indicates a reduced rate of decline relative to the previous rate of decline in the subject or the rate of decline in control patients not receiving any immunotherapy. Subjects can also be monitored for changes in autonomic dysfunction, gastrointestinal dysfunction, visual hallucination or one or more psychological symptom among other signs or symptoms.

Symptoms of subjects, for example motor symptoms such as tremor, rigidity and slowness of movement, may be monitored. Wearable systems or on-body sensors may be used to assess and quantify motor symptoms of subjects. "On-body sensors" may be used in a laboratory setting or in free-living conditions [S. Del Din, et al., J. of NeuroEngineering and Rehabilitation, 2016 13:46].

Subjects may be monitored using mobile-device-based monitoring. The mobile device may be a smartphone, smartwatch, wearable sensor, portable multimedia device or tablet computer. Built-in mobile-device sensors may be used to record daily activities of subjects. Subjects may carry a mobile-device to record their daily activities. Mobile-device-based assessments and sensors may be used for remote, passive monitoring of gait and mobility in subjects receiving treatment, for example for Parkinson's disease. (See e.g., Lipsmeier, F., et al., Mov Disord. 2017; 32 (suppl 2); W. Y. Cheng et al., 2017 *IEEE/ACM International Conference on Connected Health: Applications, Systems and Engineering Technologies (CHASE)*, Philadelphia, PA, 2017, pp. 249-250). Sensor data may be analyzed by machine learning-based activity profiling. Gait and mobility may be correlated with the MDS-UPDRS that is used in clinics to evaluate Parkinson's disease severity.

Some mobile-device-based monitoring may comprise (a) providing a subject with a mobile device programmed to receive and transmit data acquired from sensors internal and/or external to the device relating to movement deficits of a subject having or suspected of having a synucleinopathy, whereafter the subject undergoes a series of movements to reveal movement deficits, if present, and the internal or external sensors of the device acquire data relating to the movements; (b) collecting data transmitted from the mobile device; and (c) comparing the data acquired from the subjects with control data to assess presence or extent of movement deficits in the subject. In some mobile-device-based monitoring, the mobile device is programmed to receive and transmit data from at least two external sensors attached to upper and lower limbs of the subject. In some mobile-device-based monitoring, the mobile device acquires data from sensors on the upper and lower limbs of the subject. In some mobile-device-based monitoring, the mobile device is carried by the subject and acquires data from an internal sensor. In some mobile-device-based monitoring, the series of movements includes tapping the device, sitting and standing.

The present regimes can be administered concomitantly with another agent effective in treatment or prophylaxis of the disease being treated. The other agent can be another immunotherapeutic agent described herein or other agent for treating Parkinson's disease including levodopa, benzaseride, carbidopa, dopamine agonists, non-ergot dopamine agonists, catechol-O-methyl ("COMT") inhibitors such as, for example, entacopone or tolcopone, monoamine oxidase ("MAO") inhibitors, such as, for example, rasagaline, amantadine, or anticholinergic agents can be used in combination with the present regimes. Some such other agents reduce one or more symptoms of the disease without affecting causative factors.

All publications (including GenBank Accession numbers, UniProtKB/Swiss-Prot accession numbers and the like), patents and patent applications cited are herein incorporated by reference in their entirety for all purposes to the same extent as if each individual publication, patent and patent application was specifically and individually indicated to be incorporated by reference in its entirety for all purposes. In the event of any variance in sequences associated with Genbank and UniProtKB/Swiss-Prot accession numbers and the like or in website, or disease criteria of an organization, the application refers to those in effect on its effective filing date.

VIII. EXAMPLES

Example 1

Phase II Clinical Trial for an Alpha-Synuclein Antibody

Trial Design: A phase II trial is conducted for an alpha-synuclein antibody with a heavy chain variable region designated SEQ ID NO:10 and a light chain variable region designated SEQ ID NO:5 on subjects with Parkinson's disease. The trial has two treatment arms and one control arm. Subjects are randomized 1:1:1 into the arms, with N=300. The initial phase of the trial is a 52-week double blind treatment. During the initial phase of the trial, subjects do not receive other treatments Parkinson's disease (including symptomatic treatment). The subjects in one treatment arm receive a fixed dose of 1500 mg antibody intravenously every four weeks. The subjects in the other treatment arm receive 3500 mg or 4500 mg of antibody intravenously every four weeks depending on weight with subjects below 65 kg receiving the lower dosage and subjects at or above 65 kg receiving the higher dosage. The subjects in the second arm receive a loading dosage of 2000 mg and optionally additional up titration dosages at 2000 mg or above until reaching the target dose of 3500 mg or 4500 mg. Dosing is continued for one year. The trial then has an extension period in which subjects initially in the placebo group receive one of the two treatment regimes from the initial phase, and subjects from the treatment arms in the initial phase continue to receive the same treatment as previously. During the extension phase of the trial, subjects may receive systematic treatment with levodopa as well as the antibody subject of the trial, but do not receive other treatments for Parkinson's disease.

Objectives:

The primary objective is to evaluate efficacy of an alpha-synuclein antibody with a heavy chain variable region designated SEQ ID NO:10 and a light chain variable region designated SEQ ID NO:5 using the Movement Disorder Society (MDS)-sponsored revision of the Unified Parkinson's Disease Rating Scale (MDS-UPDRS).

Secondary objectives are to:

evaluate the effects of the antibody on DaT-SPECT signal and signs and symptoms of Parkinson's disease including changes in movement and cognitive deficits evaluate safety and tolerability of the antibody for up to 104 weeks, and evaluate pharmacokinetics of the antibody.

Example 2

Passive Monitoring of Early-Stage Parkinson's Disease Patient Mobility in Phase I Alpha-Synuclein Antibody Clinical Trial with Smartphone Sensors 1. Abstract—Gait and mobility in early-stage Parkinson's disease (PD) patients were measured using smartphone-based passive monitoring. In the Multiple Ascending Dose clinical trial of an alpha-synuclein antibody with a heavy chain variable region designated SEQ ID NO:10 and a light chain variable region designated SEQ ID NO:5, 44 PD patients and 35 age- and gender-matched healthy individuals performed smartphone-based assessments for up to 24 weeks and up to 6 weeks respectively. (Lipsmeier, F., et al., Mov Disord. 2017; 32 (suppl 2); W. Y. Cheng et al., 2017 *IEEE/ACM International Conference on Connected Health: Applications, Systems and Engineering Technologies* (*CHASE*), Philadelphia, PA, 2017, pp. 249-250).

For "passive monitoring", subjects carried the smartphone with them as part of their daily routine, while sensors in the smartphone recording movement data continuously. In total, over 30,000 hours of passive monitoring data were collected. To classify the sensor signal into activity profiles, a Human Activity Recognition (HAR) model was built using Deep Neural Networks (DNN) trained on previously published data. The activity profiles of the participants determined by the HAR model showed significant differences between PD patients and healthy controls in the percentage of time walking and frequency in which subjects changed positions (sitting and standing).

2. METHODS

A. Data Collection

The analysis solely focused on exploring differences between HC and PD cohorts, and did not look at antibody-related effects. In total, 24,104 hours of passive monitoring data were recorded for the PD cohort, and 8,614 hours for the HC cohort. In line with the approach of Rai, A. et al., (MobiCom'12, Aug. 22-26, 2012], accelerometer data was filtered out where the standard deviation of Euclidean norm less than 0.03 m/s2 more than 30 minutes, as during these spans smartphones were likely not carried by the subjects. This step removed 14% of the passive monitoring data.

B. HAR

A 9-layer neural network model structure was used. Similar structures have been used previously for HAR and have been shown to out-perform the traditional machine learning methods (F. J. Ordóñez and D. Roggen, Sensors 2016, 16, 115]. The HAR model was trained on two public data sets (G. M. Weiss and J. W. Lockhart, Proceedings of the AAAI-12 Workshop on Activity Context Representation: Techniques and Languages, Toronto, CA 2012; A. Stisen, et al., 13th ACM Conference on Embedded Networked Sensor Systems, Seoul, Korea, 2015) to classify six activities: walking, stairs, jogging, sitting, standing, and lying down. The continuous accelerometer data were down-sampled into 20 Hz and segmented into 4-second windows with 75% overlapping with adjacent ones.

3. RESULTS

A. Human Activity Recognition Performance Validation:

To ensure the HAR model can accurately translate the sensor data into activity profile, the performance of the model was first analyzed in the held-out validation set. The HAR model was able to correctly distinguish gait activities (walking, stairs, jogging) from stationary activities (sitting, standing, lying down) with more than 98% of accuracy. Additional validation on labeled Gait and Balance data from the trial data also showed that the HAR model was able to successfully profile the Gait segments with 96.9% of accuracy, and Balance segments with 99.5% accuracy.

B. Activity Profiles Comparison

The mobility of each subject was quantified by calculating the proportion of time when the subject engaged in gait activities (walking, stairs, jogging) over the total passive monitoring coverage time of the patient. The overall proportion of different gait activities over the total coverage for PD and HC cohorts was calculated. In the PD cohort a median was detected of 9.7% of gait spans over all coverage spans as opposed to HC cohort's 15.1%. The HC cohort had a significantly higher per-subject gait activity level than PD cohort, with Mann-Whitney test P value 2.43E-8.

C. Number of Sit-to-Stand and Stand-to-Sit Comparison

It has been observed that one manifestation of the functional impact of PD is in the sit-to-stand and stand-to-sit (STS) events (A. Zijlstra, et al., J. NeuroEngineering and Rehabilitation 2012, 9:75]. From the activity profile, the coverage-normalized STS events were calculated for each subject. Median number of STS per hour of PD patient of 1.44 was observed, which was significantly lower than HC subject's 1.74. Mann-Whitney test P value between two groups was 1.60E-8.

4. CONCLUSION

Results from this study show that it is feasible to measure gait and mobility in early-stage PD patients using smartphone-based passive monitoring. Sensor data collected during passive monitoring provides previously inaccessible, ecologically valid insights into patients' daily behavior and functioning. Significant differences were observed between PD patients and healthy controls (HC).

What is claimed is:

1. A method of treating or effecting prophylaxis of a subject having Parkinson's disease, comprising intravenously administering to the subject a dose of 1500 mg of an antibody or an antigen binding fragment thereof against alpha-synuclein at intervals of 3-5 weeks, wherein the antibody comprises a heavy chain variable region comprising SEQ ID NO:10, respectively, and a light chain comprising SEQ ID NO:5.

2. The method of claim 1, wherein the antibody comprises a heavy chain comprising SEQ ID NO:37 and a light chain comprising SEQ ID NO:32, wherein the C-terminal lysine of SEQ ID NO:37 may be absent.

3. The method of claim 1, wherein the antibody is of human IgG 1 isotype.

4. The method of claim 1, wherein the interval is 4 weeks.

5. The method of claim 1, wherein the subject receives the antibody every 4 weeks for at least 52 weeks.

6. The method of claim 5, wherein the subject has early-stage Parkinson's Disease.

7. The method of claim 1, wherein the subject is not receiving symptomatic treatment for Parkinson's disease concomitant with the antibody.

8. The method of claim 1, wherein the antibody is administered concomitantly with levodopa.

9. The method of claim 1, wherein administering the antibody is preceded by administering a loading dose of 2000 mg of the antibody and optionally uptitration at one or more subsequent dose at greater or equal to 2000 mg but less than 3500 mg until a dose of 3500 mg is reached, all doses being separated by intervals of 3-5 weeks.

10. The method of claim 1, further comprising monitoring the subject for a change in movement, cognitive deficit, autonomic dysfunction, gastrointestinal dysfunction, visual hallucination or a psychological symptom.

11. The method of claim 10, wherein the monitoring comprises (a) providing a subject with a mobile device programmed to receive and transmit data acquired from sensors internal and/or external to the device relating to movement deficits of a subject having or suspected of having a synucleinopathy, whereafter the subject undergoes a series of movements to reveal movement deficits, if present, and the internal or external sensors of the device acquire data relating to the movements;

(b) collecting data transmitted from the mobile device; and (c) comparing the data acquired from the subjects with control data to assess presence or extent of movement deficits in the subject.

12. The method of claim 11, wherein the mobile device is programmed to receive and transmit data from at least two external sensors attached to upper and lower limbs of the subject.

13. The method of claim 11, wherein the mobile device is carried by the subject and acquires data from an internal sensor.

* * * * *

SEQUENCE LISTING

<160> NUMBER OF SEQ ID NOS: 151

<210> SEQ ID NO 1
<211> LENGTH: 113
<212> TYPE: PRT
<213> ORGANISM: Artificial Sequence
<220> FEATURE:
<223> OTHER INFORMATION: Synthesized

<400> SEQUENCE: 1

Asp Ile Val Met Ser Gln Ser Pro Ser Leu Ala Val Ser Val Gly
1               5                   10                  15

Glu Lys Val Thr Met Ser Cys Lys Ser Ile Gln Thr Leu Leu Tyr Ser
            20                  25                  30

Ser Asn Gln Lys Asn Tyr Leu Ala Trp Phe Gln Gln Lys Pro Gly Gln
        35                  40                  45

Ser Pro Lys Leu Leu Ile Tyr Trp Ala Ser Ile Arg Lys Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                    85                  90                  95

Tyr Tyr Ser Tyr Pro Leu Thr Phe Gly Ala Gly Thr Lys Leu Glu Leu
            100                 105                 110

Lys

<210> SEQ ID NO 2
<211> LENGTH: 107
<212> TYPE: PRT
<213> ORGANISM: Artificial Sequence
<220> FEATURE:
<223> OTHER INFORMATION: Synthesized

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                    85                  90                  95

Thr Phe Gly Gly Gly Thr Lys Leu Glu Ile Lys
            100                 105

<210> SEQ ID NO 3
<211> LENGTH: 113
<212> TYPE: PRT
<213> ORGANISM: Artificial Sequence
<220> FEATURE:
<223> OTHER INFORMATION: Synthesized

<400> SEQUENCE: 3

Asp Ile Gln Met Thr Gln Ser Pro Ser Ser Leu Ser Ala Ser Val Gly
1               5                   10                  15

-continued

```
Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys
```

```
<210> SEQ ID NO 4
<211> LENGTH: 113
<212> TYPE: PRT
<213> ORGANISM: Artificial Sequence
<220> FEATURE:
<223> OTHER INFORMATION: Synthesized

<400> SEQUENCE: 4
```

```
Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys
```

```
<210> SEQ ID NO 5
<211> LENGTH: 113
<212> TYPE: PRT
<213> ORGANISM: Artificial Sequence
<220> FEATURE:
<223> OTHER INFORMATION: Synthesized

<400> SEQUENCE: 5
```

```
Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
```

```
                 85                  90                  95

Tyr Tyr Ser Tyr Pro Leu Thr Phe Gly Gly Gly Thr Lys Leu Glu Ile
            100                 105                 110

Lys

<210> SEQ ID NO 6
<211> LENGTH: 116
<212> TYPE: PRT
<213> ORGANISM: Artificial Sequence
<220> FEATURE:
<223> OTHER INFORMATION: Synthesized

<400> SEQUENCE: 6

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Ser Asp Lys Arg Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Glu Asp Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ser Arg Gly Gly Ala Gly Ile Asp Tyr Trp Gly Gln Gly Thr Thr Leu
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Synthesized

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ser Asp Met Asp Tyr Trp Gly Gln Gly Thr Leu Val
            100                 105                 110

Thr Val Ser Ser
        115

<210> SEQ ID NO 8
<211> LENGTH: 116
<212> TYPE: PRT
```

```
<213> ORGANISM: Artificial Sequence
<220> FEATURE:
<223> OTHER INFORMATION: Synthesized

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Gly Ala Gly Ile Asp Tyr Trp Gly Gln Gly Thr Leu Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Synthesized

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ser Arg Gly Gly Ala Gly Ile Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Synthesized

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Synthesized

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 12
<211> LENGTH: 140
<212> TYPE: PRT
<213> ORGANISM: Homo sapiens

<400> SEQUENCE: 12

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95
```

```
Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 13
<211> LENGTH: 107
<212> TYPE: PRT
<213> ORGANISM: Artificial Sequence
<220> FEATURE:
<223> OTHER INFORMATION: Synthesized

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 324
<212> TYPE: DNA
<213> ORGANISM: Artificial Sequence
<220> FEATURE:
<223> OTHER INFORMATION: Synthesized

<400> SEQUENCE: 14
cgaaactgtg gctgcaccat ctgtcttcat cttcccgcca tctgatgagc agttgaaatc      60
tggaactgcc tctgttgtgt gcctgctgaa taacttctat cccagagagg ccaaagtaca     120
gtggaaggtg gataacgccc tccaatcggg taactcccag gagagtgtca cagagcagga     180
cagcaaggac agcacctaca gcctcagcag caccctgacg ctgagcaaag cagactacga     240
gaaacacaaa gtctacgcct gcgaagtcac ccatcagggc ctgagctcgc ccgtcacaaa     300
gagctcaaca ggggagagtg ttag                                            324

<210> SEQ ID NO 15
<211> LENGTH: 330
<212> TYPE: PRT
<213> ORGANISM: Artificial Sequence
<220> FEATURE:
<223> OTHER INFORMATION: Synthesized

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

-continued

```
            35                    40                    45
Gly Val His Thr Phe Pro Ala Val Leu Gln Ser Ser Gly Leu Tyr Ser
    50                    55                    60
Leu Ser Ser Val Val Thr Val Pro Ser Ser Ser Leu Gly Thr Gln Thr
65                    70                    75                    80
Tyr Ile Cys Asn Val Asn His Lys Pro Ser Asn Thr Lys Val Asp Lys
                85                    90                    95
Arg Val Glu Pro Lys Ser Cys Asp Lys Thr His Thr Cys Pro Pro Cys
            100                   105                   110
Pro Ala Pro Glu Leu Leu Gly Gly Pro Ser Val Phe Leu Phe Pro Pro
            115                   120                   125
Lys Pro Lys Asp Thr Leu Met Ile Ser Arg Thr Pro Glu Val Thr Cys
        130                   135                   140
Val Val Val Asp Val Ser His Glu Asp Pro Glu Val Lys Phe Asn Trp
145                   150                   155                   160
Tyr Val Asp Gly Val Glu Val His Asn Val Lys Thr Lys Pro Arg Glu
                165                   170                   175
Glu Gln Tyr Asn Ser Thr Tyr Arg Val Val Ser Val Leu Thr Val Leu
            180                   185                   190
His Gln Asp Trp Leu Asn Gly Lys Glu Tyr Lys Cys Lys Val Ser Asn
        195                   200                   205
Lys Ala Leu Pro Ala Pro Ile Glu Lys Thr Ile Ser Lys Ala Lys Gly
    210                   215                   220
Gln Pro Arg Glu Pro Gln Val Tyr Thr Leu Pro Pro Ser Arg Glu Glu
225                   230                   235                   240
Met Thr Lys Asn Gln Val Ser Leu Thr Cys Leu Val Lys Gly Phe Tyr
                245                   250                   255
Pro Ser Asp Ile Ala Val Glu Trp Glu Ser Asn Gly Gln Pro Glu Asn
            260                   265                   270
Asn Tyr Lys Thr Thr Pro Pro Val Leu Asp Ser Asp Gly Ser Phe Phe
            275                   280                   285
Leu Tyr Ser Lys Leu Thr Val Asp Lys Ser Arg Trp Gln Gln Gly Asn
    290                   295                   300
Val Phe Ser Cys Ser Val Met His Glu Ala Leu His Asn His Tyr Thr
305                   310                   315                   320
Gln Lys Ser Leu Ser Leu Ser Pro Gly Lys
                325                   330
```

```
<210> SEQ ID NO 16
<211> LENGTH: 991
<212> TYPE: DNA
<213> ORGANISM: Artificial Sequence
<220> FEATURE:
<223> OTHER INFORMATION: Synthesized

<400> SEQUENCE: 16
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
acatctgcaa cgtgaatcac aagcccagca caccaaggt ggacaagaga gttgagccca     300
aatcttgtga caaaactcac acatgcccac cgtgcccagc acctgaactc ctggggggac     360
cgtcagtctt cctcttcccc ccaaaaccca aggacaccct catgatctcc cggacccctg     420
```

```
aggtcacatg cgtggtggtg gacgtgagcc acgaagaccc tgaggtcaag ttcaactggt      480
acgtggacgg cgtggaggtg cataatgtca agacaaagcc gcgggaggag cagtacaaca      540
gcacgtaccg tgtggtcagc gtcctcaccg tcctgcacca ggactggctg aatggcaagg      600
agtacaagtg caaggtctcc aacaaagccc tcccagcccc catcgagaaa accatctcca      660
aagccaaagg gcagccccga gaaccacagg tgtacacgct gcccccatcc cgggaggaga      720
tgaccaagaa ccaggtcagc ctgacctgcc tggtcaaagg cttctatccc agcgacatcg      780
cgtggagtgg gagagcaatg ggcagccgga gaacaactac aagaccacgc ctcccgtgct      840
ggactccgac ggctccttct tcctctatag caagctcacc gtggacaaga gcaggtggca      900
gcaggggaac gtcttctcat gctccgtgat gcatgaggct ctgcacaacc actacacgca      960
gaagagcctc tccctgtccc cgggtaaatg a                                      991
```

```
<210> SEQ ID NO 17
<211> LENGTH: 339
<212> TYPE: DNA
<213> ORGANISM: Artificial Sequence
<220> FEATURE:
<223> OTHER INFORMATION: Synthesized

<400> SEQUENCE: 17
gacatccaga tgacccagtc cccctcctcc ctgtccgcct ccgtgggcga ccgcgtgacc       60
atcacctgca agtccatcca gaccctgctg tactcctcca accagaagaa ctacctggcc      120
tggttccagc agaagcccgg caaggccccc aagctgctga tctactgggc ctccatccgc      180
aagtccggcg tgccctcccg cttctccggc tccggctccg gcaccgactt caccctgacc      240
atctcctccc tgcagcccga ggacttcgcc acctactact gccagcagta ctactcctac      300
cccctgacct tcggcggcgg caccaagctg gagatcaag                             339
```

```
<210> SEQ ID NO 18
<211> LENGTH: 339
<212> TYPE: DNA
<213> ORGANISM: Artificial Sequence
<220> FEATURE:
<223> OTHER INFORMATION: Synthesized

<400> SEQUENCE: 18
gacatccaga tgacccagtc cccctcctcc ctgtccgcct ccgtgggcga ccgcgtgacc       60
atcacctgca agtccatcca gaccctgctg tactcctcca accagaagaa ctacctggcc      120
tggtaccagc agaagcccgg caaggccccc aagctgctga tctactgggc ctccatccgc      180
aagtccggcg tgccctcccg cttctccggc tccggctccg gcaccgactt caccctgacc      240
atctcctccc tgcagcccga ggacttcgcc acctactact gccagcagta ctactcctac      300
cccctgacct tcggcggcgg caccaagctg gagatcaag                             339
```

```
<210> SEQ ID NO 19
<211> LENGTH: 339
<212> TYPE: DNA
<213> ORGANISM: Artificial Sequence
<220> FEATURE:
<223> OTHER INFORMATION: Synthesized

<400> SEQUENCE: 19
gacatccaga tgacccagtc cccctcctcc ctgtccgcct ccgtgggcga ccgcgtgacc       60
atcacctgca agtccatcca gaccctgctg tactcctcca accagaagaa ctacctggcc      120
```

-continued

```
tggttccagc agaagcccgg caaggccccc aagctgctga tctactgggc ctccatccgc         180
aagtccggcg tgccctcccg cttctccggc tccggctccg gcaccgactt caccctgacc         240
atctcctccc tgcagcccga ggacctggcc acctactact gccagcagta ctactcctac         300
cccctgacct tcggcggcgg caccaagctg gagatcaag                                339
```

<210> SEQ ID NO 20
<211> LENGTH: 348
<212> TYPE: DNA
<213> ORGANISM: Artificial Sequence
<220> FEATURE:
<223> OTHER INFORMATION: Synthesized

<400> SEQUENCE: 20

```
gaggtgcagc tggtggagtc cggcggcggc ctggtgcagc ccggcggctc cctgcgcctg         60
tcctgcgccg cctccggctt caccttctcc aactacggca tgtcctgggt gcgccaggcc         120
cccggcaagg gcctggagtg ggtggcctcc atctcctccg gcggcggctc cacctactac         180
cccgacaacg tgaagggccg cttcaccatc tcccgcgacg acgccaagaa ctccctgtac         240
ctgcagatga actccctgcg cgccgaggac accgccgtgt actactgctc ccgcggcggc         300
gccggcatcg actactgggg ccagggcacc ctggtgaccg tgtcctcc                      348
```

<210> SEQ ID NO 21
<211> LENGTH: 348
<212> TYPE: DNA
<213> ORGANISM: Artificial Sequence
<220> FEATURE:
<223> OTHER INFORMATION: Synthesized

<400> SEQUENCE: 21

```
gaggtgcagc tggtggagtc cggcggcggc ctggtgcagc ccggcggctc cctgcgcctg         60
tcctgcgccg cctccggctt caccttctcc aactacggca tgtcctgggt gcgccaggcc         120
cccggcaagg gcctggagtg ggtggcctcc atctcctccg gcggcggctc cacctactac         180
cccgacaacg tgaagggccg cttcaccatc tcccgcgaca cgccaagaa ctccctgtac          240 ctgcagatga actccctgcg cgccgaggac accgccgtgt actactgctc ccgcggcggc         300
gccggcatcg actactgggg ccagggcacc ctggtgaccg tgtcctcc                      348
```

<210> SEQ ID NO 22
<211> LENGTH: 348
<212> TYPE: DNA
<213> ORGANISM: Artificial Sequence
<220> FEATURE:
<223> OTHER INFORMATION: Synthesized

<400> SEQUENCE: 22

```
gaggtgcagc tggtggagtc cggcggcggc ctggtgcagc ccggcggctc cctgcgcctg         60
tcctgcgccg cctccggctt caccttctcc aactacggca tgtcctgggt gcgccaggcc         120
cccggcaagg gcctggagtg ggtggcctcc atctcctccg gcggcggctc cacctactac         180
cccgacaacg tgaagggccg cttcaccatc tcccgcgacg acgccaagaa ctccctgtac         240
ctgcagatga actccctgcg cgccgaggac accgccgtgt actactgcgc ccgcggcggc         300
gccggcatcg actactgggg ccagggcacc ctggtgaccg tgtcctcc                      348
```

<210> SEQ ID NO 23
<211> LENGTH: 348
<212> TYPE: DNA
<213> ORGANISM: Artificial Sequence -continued

```
<220> FEATURE:
<223> OTHER INFORMATION: Synthesized

<400> SEQUENCE: 23
gaggtgcagc tggtggagtc cggcggcggc ctggtgcagc ccggcggctc cctgcgcctg      60
tcctgcgccg cctccggctt caccttctcc aactacggca tgtcctgggt gcgccaggcc     120
cccggcaagg gcctggagtg ggtggcctcc atctcctccg gcggcggctc cacctactac     180
cccgacaacg tgaagggccg cttcaccatc tcccgcgaca cgccaagaa ctccctgtac      240 ctgcagatga actccctgcg cgccgaggac accgccgtgt actactgcgc cgcgcggcggc    300 gccggcatcg actactgggg ccagggcacc ctggtgaccg tgtcctcc                 348

<210> SEQ ID NO 24
<211> LENGTH: 22
<212> TYPE: PRT
<213> ORGANISM: Artificial Sequence
<220> FEATURE:
<223> OTHER INFORMATION: Synthesized

<400> SEQUENCE: 24

Met Asp Met Arg Val Pro Ala Gln Leu Leu Gly Leu Leu Met Leu Trp
1               5                   10                  15

Val Ser Gly Ser Ser Gly
            20

<210> SEQ ID NO 25
<211> LENGTH: 66
<212> TYPE: DNA
<213> ORGANISM: Artificial Sequence
<220> FEATURE:
<223> OTHER INFORMATION: Synthesized

<400> SEQUENCE: 25
atggacatgc gcgtgcccgc ccagctgctg ggcctgctga tgctgtgggt gtccggctcc      60
tccggc                                                                66

<210> SEQ ID NO 26
<211> LENGTH: 19
<212> TYPE: PRT
<213> ORGANISM: Artificial Sequence
<220> FEATURE:
<223> OTHER INFORMATION: Synthesized

<400> SEQUENCE: 26

Met Glu Phe Gly Leu Ser Trp Leu Phe Leu Val Ala Ile Leu Lys Gly
1               5                   10                  15

Val Gln Cys

<210> SEQ ID NO 27
<211> LENGTH: 57
<212> TYPE: DNA
<213> ORGANISM: Artificial Sequence
<220> FEATURE:
<223> OTHER INFORMATION: Synthesized

<400> SEQUENCE: 27
atggagttcg gcctgtcctg gctgttcctg gtggccatcc tgaagggcgt gcagtgc        57

<210> SEQ ID NO 28
<211> LENGTH: 113
<212> TYPE: PRT
<213> ORGANISM: Artificial Sequence
```

```
<220> FEATURE:
<223> OTHER INFORMATION: Synthesized
<220> FEATURE:
<221> NAME/KEY: VARIANT
<222> LOCATION: (42)..(42)
<223> OTHER INFORMATION: Xaa = Y or F
<220> FEATURE:
<221> NAME/KEY: VARIANT
<222> LOCATION: (89)..(89)
<223> OTHER INFORMATION: Xaa = F or L

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Xaa Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Xaa Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 29
<211> LENGTH: 116
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (74)..(74)
<223> OTHER INFORMATION: Xaa = N or D
<220> FEATURE:
<221> NAME/KEY: VARIANT
<222> LOCATION: (97)..(97)
<223> OTHER INFORMATION: Xaa = A or S

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Xaa Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Xaa Arg Gly Gly Ala Gly Ile Asp Tyr Trp Gly Gln Gly Thr Leu Val
            100                 105                 110

Thr Val Ser Ser
        115
```

```
<210> SEQ ID NO 30
<211> LENGTH: 106
<212> TYPE: PRT
<213> ORGANISM: Artificial Sequence
<220> FEATURE:
<223> OTHER INFORMATION: Synthesized

<400> SEQUENCE: 30

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 31
<211> LENGTH: 321
<212> TYPE: DNA
<213> ORGANISM: Artificial Sequence
<220> FEATURE:
<223> OTHER INFORMATION: Synthesized

<400> SEQUENCE: 31
aactgtggct gcaccatctg tcttcatctt cccgccatct gatgagcagt tgaaatctgg      60
aactgcctct gttgtgtgcc tgctgaataa cttctatccc agagaggcca agtacagtg      120 gaaggtggat aacgccctcc aatcgggtaa ctcccaggag agtgtcacag agcaggacag      180
caaggacagc acctacagcc tcagcagcac cctgacgctg agcaaagcag actacgagaa      240
acacaaagtc tacgcctgcg aagtcacccca tcagggcctg agctcgcccg tcacaaagag      300
ctcaacaggg gagagtgtta g                                                321

<210> SEQ ID NO 32
<211> LENGTH: 220
<212> TYPE: PRT
<213> ORGANISM: Artificial Sequence
<220> FEATURE:
<223> OTHER INFORMATION: Synthesized

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95
```

```
Tyr Tyr Ser Tyr Pro Leu Thr Phe Gly Gly Gly Thr Lys Leu Glu Ile
            100             105             110

Lys Arg Thr Val Ala Ala Pro Ser Val Phe Ile Phe Pro Pro Ser Asp
            115             120             125

Glu Gln Leu Lys Ser Gly Thr Ala Ser Val Val Cys Leu Leu Asn Asn
    130             135             140

Phe Tyr Pro Arg Glu Ala Lys Val Gln Trp Lys Val Asp Asn Ala Leu
145             150             155             160

Gln Ser Gly Asn Ser Gln Glu Ser Val Thr Glu Gln Asp Ser Lys Asp
            165             170             175

Ser Thr Tyr Ser Leu Ser Ser Thr Leu Thr Leu Ser Lys Ala Asp Tyr
            180             185             190

Glu Lys His Lys Val Tyr Ala Cys Glu Val Thr His Gln Gly Leu Ser
            195             200             205

Ser Pro Val Thr Lys Ser Phe Asn Arg Gly Glu Cys
    210             215             220

<210> SEQ ID NO 33
<211> LENGTH: 219
<212> TYPE: PRT
<213> ORGANISM: Artificial Sequence
<220> FEATURE:
<223> OTHER INFORMATION: Synthesized

<400> SEQUENCE: 33

Asp Ile Gln Met Thr Gln Ser Pro Ser Ser Leu Ser Ala Ser Val Gly
1               5               10              15

Asp Arg Val Thr Ile Thr Cys Lys Ser Ile Gln Thr Leu Leu Tyr Ser
            20              25              30

Ser Asn Gln Lys Asn Tyr Leu Ala Trp Phe Gln Gln Lys Pro Gly Lys
        35              40              45

Ala Pro Lys Leu Leu Ile Tyr Trp Ala Ser Ile Arg Lys Ser Gly Val
    50              55              60

Pro Ser Arg Phe Ser Gly Ser Gly Ser Gly Thr Asp Phe Thr Leu Thr
65              70              75              80

Ile Ser Ser Leu Gln Pro Glu Asp Leu Ala Thr Tyr Tyr Cys Gln Gln
            85              90              95

Tyr Tyr Ser Tyr Pro Leu Thr Phe Gly Gly Gly Thr Lys Leu Glu Ile
            100             105             110

Lys Thr Val Ala Ala Pro Ser Val Phe Ile Phe Pro Pro Ser Asp Glu
            115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
            180             185             190

Lys His Lys Val Tyr Ala Cys Glu Val Thr His Gln Gly Leu Ser Ser
            195             200             205

Pro Val Thr Lys Ser Phe Asn Arg Gly Glu Cys
    210             215

<210> SEQ ID NO 34
```

-continued

```
<211> LENGTH: 446
<212> TYPE: PRT
<213> ORGANISM: Artificial Sequence
<220> FEATURE:
<223> OTHER INFORMATION: Synthesized

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Val Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

-continued

```
Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 35
<211> LENGTH: 330
<212> TYPE: PRT
<213> ORGANISM: Artificial Sequence
<220> FEATURE:
<223> OTHER INFORMATION: Synthesized

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300
```

-continued

```
Val Phe Ser Cys Ser Val Met His Glu Ala Leu His Asn His Tyr Thr
305             310             315             320

Gln Lys Ser Leu Ser Leu Ser Pro Gly Lys
                325             330

<210> SEQ ID NO 36
<211> LENGTH: 446
<212> TYPE: PRT
<213> ORGANISM: Artificial Sequence
<220> FEATURE:
<223> OTHER INFORMATION: Synthesized

<400> SEQUENCE: 36

Glu Val Gln Leu Val Glu Ser Gly Gly Gly Leu Val Gln Pro Gly Gly
1               5               10              15

Ser Leu Arg Leu Ser Cys Ala Ala Ser Gly Phe Thr Phe Ser Asn Tyr
            20              25              30

Gly Met Ser Trp Val Arg Gln Ala Pro Gly Lys Gly Leu Glu Trp Val
        35              40              45

Ala Ser Ile Ser Ser Gly Gly Gly Ser Thr Tyr Tyr Pro Asp Asn Val
    50              55              60

Lys Gly Arg Phe Thr Ile Ser Arg Asp Asp Ala Lys Asn Ser Leu Tyr
65              70              75              80

Leu Gln Met Asn Ser Leu Arg Ala Glu Asp Thr Ala Val Tyr Tyr Cys
                85              90              95

Ala Arg Gly Gly Ala Gly Ile Asp Tyr Trp Gly Gln Gly Thr Leu Val
            100             105             110

Thr Val Ser Ser Ala Ser Thr Lys Gly Pro Ser Val Phe Pro Leu Ala
        115             120             125

Pro Ser Ser Lys Ser Thr Ser Gly Gly Thr Ala Ala Leu Gly Cys Leu
    130             135             140

Val Lys Asp Tyr Phe Pro Glu Pro Val Thr Val Ser Trp Asn Ser Gly
145             150             155             160

Ala Leu Thr Ser Gly Val His Thr Phe Pro Ala Val Leu Gln Ser Ser
            165             170             175

Gly Leu Tyr Ser Leu Ser Ser Val Val Thr Val Pro Ser Ser Ser Leu
            180             185             190

Gly Thr Gln Thr Tyr Ile Cys Asn Val Asn His Lys Pro Ser Asn Thr
            195             200             205

Lys Val Asp Lys Arg Val Glu Pro Lys Ser Cys Asp Lys Thr His Thr
    210             215             220

Cys Pro Pro Cys Pro Ala Pro Glu Leu Leu Gly Gly Pro Ser Val Phe
225             230             235             240

Leu Phe Pro Pro Lys Pro Lys Asp Thr Leu Met Ile Ser Arg Thr Pro
            245             250             255

Glu Val Thr Cys Val Val Val Asp Val Ser His Glu Asp Pro Glu Val
            260             265             270

Lys Phe Asn Trp Tyr Val Asp Gly Val Glu Val His Asn Val Lys Thr
        275             280             285

Lys Pro Arg Glu Glu Gln Tyr Asn Ser Thr Tyr Arg Val Val Ser Val
    290             295             300

Leu Thr Val Leu His Gln Asp Trp Leu Asn Gly Lys Glu Tyr Lys Cys
305             310             315             320

Lys Val Ser Asn Lys Ala Leu Pro Ala Pro Ile Glu Lys Thr Ile Ser
            325             330             335
```

```
Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 37
<211> LENGTH: 446
<212> TYPE: PRT
<213> ORGANISM: Artificial Sequence
<220> FEATURE:
<223> OTHER INFORMATION: Synthesized

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
            35                  40                  45

Ala Ser Ile Ser Ser Gly Gly Ser Thr Tyr Tyr Pro Asp Asn Val
            50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Arg Val Glu Pro Lys Ser Cys Asp Lys Thr His Thr
            210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445
```

<210> SEQ ID NO 38
<211> LENGTH: 345
<212> TYPE: DNA
<213> ORGANISM: Artificial Sequence
<220> FEATURE:
<223> OTHER INFORMATION: Synthesized

<400> SEQUENCE: 38

```
caggtccagc tgcagcagtc tgggggctgaa ctggcaaaac ctggggacctc agtgcagatg      60 tcctgcaagg cttctggcta cacctttact aattactgga tgaactggat aaaagcgagg     120
cctggacagg gtctggaatg gattgggggct actaatccta caatggtta tactgactac     180 aatcagaggt tcaaggacaa ggccatatta actgcagaca atcctccaa tacagcctac     240 atgcacctga gcagcctgac atctgaagac tctgcagtct atttctgtgc aagtgggggg     300
cacttggctt actggggcca ggggactgtg gtcactgtct ctgca                      345
```

<210> SEQ ID NO 39
<211> LENGTH: 115
<212> TYPE: PRT
<213> ORGANISM: Artificial Sequence
<220> FEATURE:
<223> OTHER INFORMATION: Synthesized

<400> SEQUENCE: 39

```
Gln Val Gln Leu Gln Gln Ser Gly Ala Glu Leu Ala Lys Pro Gly Thr
1               5                   10                  15

Ser Val Gln Met Ser Cys Lys Ala Ser Gly Tyr Thr Phe Thr Asn Tyr
                20                  25                  30

Trp Met Asn Trp Ile Lys Ala Arg Pro Gly Gln Gly Leu Glu Trp Ile
        35                  40                  45

Gly Ala Thr Asn Pro Asn Asn Gly Tyr Thr Asp Tyr Asn Gln Arg Phe
```

```
          50               55               60

Lys Asp Lys Ala Ile Leu Thr Ala Asp Lys Ser Ser Asn Thr Ala Tyr
65                  70               75                  80

Met His Leu Ser Ser Leu Thr Ser Glu Asp Ser Ala Val Tyr Phe Cys
                85               90                  95

Ala Ser Gly Gly His Leu Ala Tyr Trp Gly Gln Gly Thr Val Val Thr
            100              105              110

Val Ser Ala
        115
```

```
<210> SEQ ID NO 40
<211> LENGTH: 57
<212> TYPE: DNA
<213> ORGANISM: Artificial Sequence
<220> FEATURE:
<223> OTHER INFORMATION: Synthesized

<400> SEQUENCE: 40
atggaaaggc actggatctt tctcttcctg ttatcagtaa ctggaggtgt ccactcc        57
```

```
<210> SEQ ID NO 41
<211> LENGTH: 19
<212> TYPE: PRT
<213> ORGANISM: Artificial Sequence
<220> FEATURE:
<223> OTHER INFORMATION: Synthesized

<400> SEQUENCE: 41

Met Glu Arg His Trp Ile Phe Leu Phe Leu Leu Ser Val Thr Gly Gly
1               5               10                  15

Val His Ser
```

```
<210> SEQ ID NO 42
<211> LENGTH: 336
<212> TYPE: DNA
<213> ORGANISM: Artificial Sequence
<220> FEATURE:
<223> OTHER INFORMATION: Synthesized

<400> SEQUENCE: 42
gatgttgtga tgacccaaat tccactctac ctgtctgtca gtcctggaga tcaagcctcc      60
atctcttgca gatctagtca gagccttttc catagtaaag aaacaccta tttacattgg     120 tatctgcaga agccaggcca gtctccaaag ctcctgatca cagggtttc caaccgattt      180 tctggggtcc cagacaggtt cagtggcagt ggatcaggga cagatttcac actcaagatc     240
agcggagtgg aggctgaaga tctgggagtt tatttctgtt ctcaaagtgc acatgttccg     300
tggacgttcg gtggaggcac caagctggaa atcaga                              336
```

```
<210> SEQ ID NO 43
<211> LENGTH: 112
<212> TYPE: PRT
<213> ORGANISM: Artificial Sequence
<220> FEATURE:
<223> OTHER INFORMATION: Synthesized

<400> SEQUENCE: 43

Asp Val Val Met Thr Gln Ile Pro Leu Tyr Leu Ser Val Ser Pro Gly
1               5               10                  15

Asp Gln Ala Ser Ile Ser Cys Arg Ser Ser Gln Ser Leu Phe His Ser
            20               25               30
```

```
Lys Gly Asn Thr Tyr Leu His Trp Tyr Leu Gln Lys Pro Gly Gln Ser
        35                  40                  45

Pro Lys Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Phe Cys Ser Gln Ser
                85                  90                  95

Ala His Val Pro Trp Thr Phe Gly Gly Gly Thr Lys Leu Glu Ile Arg
            100                 105                 110

<210> SEQ ID NO 44
<211> LENGTH: 60
<212> TYPE: DNA
<213> ORGANISM: Artificial Sequence
<220> FEATURE:
<223> OTHER INFORMATION: Synthesized

<400> SEQUENCE: 44
atgaagttgc ctgttaggct gttggtgctg atgttctgga ttcctgcttc cagcagtgat        60

<210> SEQ ID NO 45
<211> LENGTH: 20
<212> TYPE: PRT
<213> ORGANISM: Artificial Sequence
<220> FEATURE:
<223> OTHER INFORMATION: Synthesized

<400> SEQUENCE: 45

Met Lys Leu Pro Val Arg Leu Leu Val Leu Met Phe Trp Ile Pro Ala
1               5                   10                  15

Ser Ser Ser Asp
            20

<210> SEQ ID NO 46
<211> LENGTH: 12
<212> TYPE: PRT
<213> ORGANISM: Artificial Sequence
<220> FEATURE:
<223> OTHER INFORMATION: Synthesized

<400> SEQUENCE: 46

Val Asp Pro Asp Asn Glu Ala Tyr Glu Gly Gly Cys
1               5                   10

<210> SEQ ID NO 47
<211> LENGTH: 5
<212> TYPE: PRT
<213> ORGANISM: Artificial Sequence
<220> FEATURE:
<223> OTHER INFORMATION: Synthesized

<400> SEQUENCE: 47

Asn Tyr Trp Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: Synthesized

<400> SEQUENCE: 48
```

```
Ala Thr Asn Pro Asn Asn Gly Tyr Thr Asp Tyr Asn Gln Arg Phe Lys
1               5                   10                  15

Asp

<210> SEQ ID NO 49
<211> LENGTH: 6
<212> TYPE: PRT
<213> ORGANISM: Artificial Sequence
<220> FEATURE:
<223> OTHER INFORMATION: Synthesized

<400> SEQUENCE: 49

Gly Gly His Leu Ala Tyr
1               5

<210> SEQ ID NO 50
<211> LENGTH: 16
<212> TYPE: PRT
<213> ORGANISM: Artificial Sequence
<220> FEATURE:
<223> OTHER INFORMATION: Synthesized

<400> SEQUENCE: 50

Arg Ser Ser Gln Ser Leu Phe His Ser Lys Gly Asn Thr Tyr Leu His
1               5                   10                  15

<210> SEQ ID NO 51
<211> LENGTH: 7
<212> TYPE: PRT
<213> ORGANISM: Artificial Sequence
<220> FEATURE:
<223> OTHER INFORMATION: Synthesized

<400> SEQUENCE: 51

Arg Val Ser Asn Arg Phe Ser
1               5

<210> SEQ ID NO 52
<211> LENGTH: 9
<212> TYPE: PRT
<213> ORGANISM: Artificial Sequence
<220> FEATURE:
<223> OTHER INFORMATION: Synthesized

<400> SEQUENCE: 52

Ser Gln Ser Ala His Val Pro Trp Thr
1               5

<210> SEQ ID NO 53
<211> LENGTH: 402
<212> TYPE: DNA
<213> ORGANISM: Artificial Sequence
<220> FEATURE:
<223> OTHER INFORMATION: Synthesized

<400> SEQUENCE: 53
atggaaaggc actggatctt tctcttcctg ttatcagtaa ctggaggtgt ccactcccag      60
gtccagctgc agcagtctgg ggctgaactg gcaaaacctg ggacctcagt gcagatgtcc     120
tgcaaggctt ctggctacac ctttactaat tactggatga actggataaa agcgaggcct     180
ggacagggtc tggaatggat tggggctact aatcctaaca tggttatac tgactacaat      240 cagaggttca aggacaaggc catattaact gcagacaaat cctccaatac agcctacatg     300
cacctgagca gcctgacatc tgaagactct gcagtctatt tctgtgcaag tgggggggcac    360
```

-continued

```
ttggcttact ggggccaggg gactgtggtc actgtctctg ca                    402
```

<210> SEQ ID NO 54
<211> LENGTH: 134
<212> TYPE: PRT
<213> ORGANISM: Artificial Sequence
<220> FEATURE:
<223> OTHER INFORMATION: Synthesized

<400> SEQUENCE: 54

```
Met Glu Arg His Trp Ile Phe Leu Phe Leu Leu Ser Val Thr Gly Gly
1               5                   10                  15

Val His Ser Gln Val Gln Leu Gln Gln Ser Gly Ala Glu Leu Ala Lys
            20                  25                  30

Pro Gly Thr Ser Val Gln Met Ser Cys Lys Ala Ser Gly Tyr Thr Phe
        35                  40                  45

Thr Asn Tyr Trp Met Asn Trp Ile Lys Ala Arg Pro Gly Gln Gly Leu
    50                  55                  60

Glu Trp Ile Gly Ala Thr Asn Pro Asn Asn Gly Tyr Thr Asp Tyr Asn
65                  70                  75                  80

Gln Arg Phe Lys Asp Lys Ala Ile Leu Thr Ala Asp Lys Ser Ser Asn
                85                  90                  95

Thr Ala Tyr Met His Leu Ser Ser Leu Thr Ser Glu Asp Ser Ala Val
            100                 105                 110

Tyr Phe Cys Ala Ser Gly Gly His Leu Ala Tyr Trp Gly Gln Gly Thr
            115                 120                 125

Val Val Thr Val Ser Ala
        130
```

<210> SEQ ID NO 55
<211> LENGTH: 393
<212> TYPE: DNA
<213> ORGANISM: Artificial Sequence
<220> FEATURE:
<223> OTHER INFORMATION: Synthesized

<400> SEQUENCE: 55

```
atgaagttgc ctgttaggct gttggtgctg atgttctgga ttcctgcttc cagcagtgat     60
gttgtgatga cccaaattcc actctacctg tctgtcagtc ctggagatca agcctccatc    120
tcttgcagat ctagtcagag cctttttccat agtaaaggaa acacctattt acattggtat    180
ctgcagaagc caggccagtc tccaaagctc ctgatcaaca gggtttccaa ccgattttct    240
ggggtcccag acaggttcag tggcagtgga tcagggacag atttcacact caagatcagc    300
ggagtggagg ctgaagatct gggagtttat ttctgttctc aaagtgcaca tgttccgtgg    360
acgttcggtg gaggcaccaa gctggaaatc aga                                 393
```

<210> SEQ ID NO 56
<211> LENGTH: 131
<212> TYPE: PRT
<213> ORGANISM: Artificial Sequence
<220> FEATURE:
<223> OTHER INFORMATION: Synthesized

<400> SEQUENCE: 56

```
Met Lys Leu Pro Val Arg Leu Leu Val Leu Met Phe Trp Ile Pro Ala
1               5                   10                  15

Ser Ser Ser Asp Val Val Met Thr Gln Ile Pro Leu Tyr Leu Ser Val
            20                  25                  30
```

-continued

```
Ser Pro Gly Asp Gln Ala Ser Ile Ser Cys Arg Ser Ser Gln Ser Leu
    35              40              45

Phe His Ser Lys Gly Asn Thr Tyr Leu His Trp Tyr Leu Gln Lys Pro
    50              55              60

Gly Gln Ser Pro Lys Leu Leu Ile Asn Arg Val Ser Asn Arg Phe Ser
65              70              75              80

Gly Val Pro Asp Arg Phe Ser Gly Ser Gly Ser Gly Thr Asp Phe Thr
                85              90              95

Leu Lys Ile Ser Gly Val Glu Ala Glu Asp Leu Gly Val Tyr Phe Cys
            100             105             110

Ser Gln Ser Ala His Val Pro Trp Thr Phe Gly Gly Gly Thr Lys Leu
        115             120             125

Glu Ile Arg
    130
```

```
<210> SEQ ID NO 57
<211> LENGTH: 118
<212> TYPE: PRT
<213> ORGANISM: Artificial Sequence
<220> FEATURE:
<223> OTHER INFORMATION: Synthesized

<400> SEQUENCE: 57

Gln Val Gln Leu Val Gln Ser Gly Ala Glu Val Lys Lys Pro Gly Ser
1               5               10              15

Ser Val Lys Val Ser Cys Lys Ala Ser Gly Gly Thr Phe Asn Asn Tyr
            20              25              30

Ala Ile Asn Trp Val Arg Gln Ala Pro Gly Gln Gly Leu Glu Trp Met
        35              40              45

Gly Gly Ile Ile Pro Ile Phe Gly Thr Thr Thr Tyr Ala Gln Lys Phe
    50              55              60

Gln Gly Arg Val Thr Ile Thr Ala Asp Glu Ser Thr Asn Thr Ala Tyr
65              70              75              80

Met Glu Leu Ser Ser Leu Arg Ser Glu Asp Thr Ala Val Tyr Tyr Cys
                85              90              95

Ala Arg Glu Gly Asn Leu Asn Trp Leu Asp Pro Trp Gly Gln Gly Thr
            100             105             110

Leu Val Thr Val Ser Ser
        115
```

```
<210> SEQ ID NO 58
<211> LENGTH: 115
<212> TYPE: PRT
<213> ORGANISM: Artificial Sequence
<220> FEATURE:
<223> OTHER INFORMATION: Synthesized

<400> SEQUENCE: 58

Gln Val Gln Leu Val Gln Ser Gly Ala Glu Leu Lys Lys Pro Gly Ser
1               5               10              15

Ser Val Lys Val Ser Cys Lys Ala Ser Gly Tyr Thr Phe Thr Asn Tyr
            20              25              30

Trp Met Asn Trp Val Arg Gln Ala Pro Gly Gln Gly Leu Glu Trp Ile
        35              40              45

Gly Ala Thr Asn Pro Asn Asn Gly Tyr Thr Asp Tyr Asn Gln Arg Phe
    50              55              60

Lys Asp Arg Ala Thr Leu Thr Ala Asp Lys Ser Thr Asn Thr Ala Tyr
65              70              75              80
```

```
Met Glu Leu Ser Ser Leu Arg Ser Glu Asp Thr Ala Val Tyr Tyr Cys
            85                  90                  95

Ala Arg Gly Gly His Leu Ala Tyr Trp Gly Gln Gly Thr Leu Val Thr
            100                 105                 110

Val Ser Ser
        115

<210> SEQ ID NO 59
<211> LENGTH: 115
<212> TYPE: PRT
<213> ORGANISM: Artificial Sequence
<220> FEATURE:
<223> OTHER INFORMATION: Synthesized

<400> SEQUENCE: 59

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly His Leu Ala Tyr Trp Gly Gln Gly Thr Leu Val Thr
            100                 105                 110

Val Ser Ser
        115

<210> SEQ ID NO 60
<211> LENGTH: 115
<212> TYPE: PRT
<213> ORGANISM: Artificial Sequence
<220> FEATURE:
<223> OTHER INFORMATION: Synthesized

<400> SEQUENCE: 60

Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Phe Cys
            85                  90                  95

Ala Ser Gly Gly His Leu Ala Tyr Trp Gly Gln Gly Thr Leu Val Thr
            100                 105                 110

Val Ser Ser
        115
```

<210> SEQ ID NO 61
<211> LENGTH: 115
<212> TYPE: PRT
<213> ORGANISM: Artificial Sequence
<220> FEATURE:
<223> OTHER INFORMATION: Synthesized

<400> SEQUENCE: 61

```
Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Ala Thr Leu Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser
        115
```

<210> SEQ ID NO 62
<211> LENGTH: 115
<212> TYPE: PRT
<213> ORGANISM: Artificial Sequence
<220> FEATURE:
<223> OTHER INFORMATION: Synthesized

<400> SEQUENCE: 62

```
Gln Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Asn Tyr
            20                  25                  30

Trp Met Asn Trp Val Arg Gln Ala Pro Gly Gln Gly Leu Glu Trp Ile
        35                  40                  45

Gly Ala Thr Asn Pro Asn Asn Gly Tyr Thr Asp Tyr Asn Gln Arg Phe
    50                  55                  60

Lys Asp Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ser Gly Gly His Leu Ala Tyr Trp Gly Gln Gly Thr Leu Val Thr
            100                 105                 110

Val Ser Ser
        115
```

<210> SEQ ID NO 63
<211> LENGTH: 402
<212> TYPE: DNA
<213> ORGANISM: Artificial Sequence
<220> FEATURE:
<223> OTHER INFORMATION: Synthesized

<400> SEQUENCE: 63
atggagttcg gcctgtcctg gctgttcctg gtggccatcc tgaagggcgt gcagtgccag      60

```
gtgcagctgg tgcagtccgg cgccgagctg aagaagcccg gctcctccgt gaaggtgtcc        120
tgcaaggcct ccggctacac cttcaccaac tactggatga actgggtgcg ccaggccccc        180
ggccagggcc tggagtggat cggcgccacc aacccccaaca acggctacac cgactacaac       240
cagcgcttca aggaccgcgc caccctgacc gccgacaagt ccaccaacac cgcctacatg        300
gagctgtcct ccctgcgctc cgaggacacc gccgtgtact actgcgcccg cggcggccac        360
ctggcctact ggggccaggg caccctggtg accgtgtcct cc                          402
```

```
<210> SEQ ID NO 64
<211> LENGTH: 402
<212> TYPE: DNA
<213> ORGANISM: Artificial Sequence
<220> FEATURE:
<223> OTHER INFORMATION: Synthesized

<400> SEQUENCE: 64
```

```
atggagttcg gcctgtcctg gctgttcctg gtggccatcc tgaagggcgt gcagtgccag         60
gtgcagctgg tgcagtccgg cgccgagctg aagaagcccg gctcctccgt gaaggtgtcc        120
tgcaaggcct ccggctacac cttcaccaac tactggatga actgggtgcg ccaggccccc        180
ggccagggcc tggagtggat cggcgccacc aacccccaaca acggctacac cgactacaac       240
cagcgcttca aggaccgcgt gaccatcacc gccgacaagt ccaccaacac cgcctacatg        300
gagctgtcct ccctgcgctc cgaggacacc gccgtgtact actgcgcccg cggcggccac        360
ctggcctact ggggccaggg caccctggtg accgtgtcct cc                          402
```

```
<210> SEQ ID NO 65
<211> LENGTH: 402
<212> TYPE: DNA
<213> ORGANISM: Artificial Sequence
<220> FEATURE:
<223> OTHER INFORMATION: Synthesized

<400> SEQUENCE: 65
```

```
atggagttcg gcctgtcctg gctgttcctg gtggccatcc tgaagggcgt gcagtgccag         60
gtgcagctgg tgcagtccgg cgccgagctg aagaagcccg gctcctccgt gaaggtgtcc        120
tgcaaggcct ccggctacac cttcaccaac tactggatga actgggtgcg ccaggccccc        180
ggccagggcc tggagtggat cggcgccacc aacccccaaca acggctacac cgactacaac       240
cagcgcttca aggaccgcgc caccctgacc gccgacaagt ccaccaacac cgcctacatg        300
gagctgtcct ccctgcgctc cgaggacacc gccgtgtact tctgcgcctc cggcggccac        360
ctggcctact ggggccaggg caccctggtg accgtgtcct cc                          402
```

```
<210> SEQ ID NO 66
<211> LENGTH: 402
<212> TYPE: DNA
<213> ORGANISM: Artificial Sequence
<220> FEATURE:
<223> OTHER INFORMATION: Synthesized

<400> SEQUENCE: 66
```

```
atggagttcg gcctgtcctg gctgttcctg gtggccatcc tgaagggcgt gcagtgccag         60
gtgcagctgg tgcagtccgg cgccgagctg aagaagcccg gctcctccgt gaaggtgtcc        120
tgcaaggcct ccggctacac cttcaccaac tactggatga actgggtgcg ccaggccccc        180
ggccagggcc tggagtggat cggcgccacc aacccccaaca acggctacac cgactacaac       240
cagcgcttca aggaccgcgc caccctgacc gccgacaagt ccaccaacac cgcctacatg        300
```

-continued

```
gagctgtcct ccctgcgctc cgaggacacc gccgtgtact actgcgcctc cggcggccac      360
ctggcctact ggggccaggg caccctggtg accgtgtcct cc                          402

<210> SEQ ID NO 67
<211> LENGTH: 402
<212> TYPE: DNA
<213> ORGANISM: Artificial Sequence
<220> FEATURE:
<223> OTHER INFORMATION: Synthesized

<400> SEQUENCE: 67
atggagttcg gcctgtcctg gctgttcctg gtggccatcc tgaagggcgt gcagtgccag       60
gtgcagctgg tgcagtccgg cgccgagctg aagaagcccg gctcctccgt gaaggtgtcc      120
tgcaaggcct ccggctacac cttcaccaac tactggatga actgggtgcg ccaggccccc      180
ggccagggcc tggagtggat cggcgccacc aaccccaaca acggctacac cgactacaac      240
cagcgcttca aggaccgcgt gaccatcacc gccgacaagt ccaccaacac cgcctacatg      300
gagctgtcct ccctgcgctc cgaggacacc gccgtgtact actgcgccag cggcggccac      360
ctggcctact ggggccaggg caccctggtg accgtgtcct cc                          402

<210> SEQ ID NO 68
<211> LENGTH: 112
<212> TYPE: PRT
<213> ORGANISM: Artificial Sequence
<220> FEATURE:
<223> OTHER INFORMATION: Synthesized

<400> SEQUENCE: 68

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gly Gly Thr Lys Val Glu Ile Lys
            100                 105                 110

<210> SEQ ID NO 69
<211> LENGTH: 112
<212> TYPE: PRT
<213> ORGANISM: Artificial Sequence
<220> FEATURE:
<223> OTHER INFORMATION: Synthesized

<400> SEQUENCE: 69

Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45
```

-continued

```
Pro Lys Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
                100                 105                 110

<210> SEQ ID NO 70
<211> LENGTH: 112
<212> TYPE: PRT
<213> ORGANISM: Artificial Sequence
<220> FEATURE:
<223> OTHER INFORMATION: Synthesized

<400> SEQUENCE: 70

Asp Ile Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
                20                  25                  30

Lys Gly Asn Thr Tyr Leu His Trp Tyr Leu Gln Lys Pro Gly Gln Ser
            35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
                100                 105                 110

<210> SEQ ID NO 71
<211> LENGTH: 112
<212> TYPE: PRT
<213> ORGANISM: Artificial Sequence
<220> FEATURE:
<223> OTHER INFORMATION: Synthesized

<400> SEQUENCE: 71

Asp Val Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
                20                  25                  30

Lys Gly Asn Thr Tyr Leu His Trp Tyr Leu Gln Lys Pro Gly Gln Ser
            35                  40                  45

Pro Gln Leu Leu Ile Asn Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
                100                 105                 110

<210> SEQ ID NO 72
<211> LENGTH: 112
<212> TYPE: PRT
<213> ORGANISM: Artificial Sequence
```

-continued

<220> FEATURE:
<223> OTHER INFORMATION: Synthesized

<400> SEQUENCE: 72

```
Asp Ile Val Met Thr Gln Ser Pro Leu Ser Leu Ser Val Ser Pro Gly
1               5                   10                  15

Glu Pro Ala Ser Ile Ser Cys Arg Ser Ser Gln Ser Leu Phe His Ser
            20                  25                  30

Lys Gly Asn Thr Tyr Leu His Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Ala His Val Pro Trp Thr Phe Gly Gly Gly Thr Lys Val Glu Ile Lys
            100                 105                 110
```

<210> SEQ ID NO 73
<211> LENGTH: 402
<212> TYPE: DNA
<213> ORGANISM: Artificial Sequence
<220> FEATURE:
<223> OTHER INFORMATION: Synthesized

<400> SEQUENCE: 73

```
atggacatgc gcgtgcccgc ccagctgctg ggcctgctga tgctgtgggt gtccggctcc      60
tccggcgacg tggtgatgac ccagtccccc ctgtccctgt ccgtgtcccc cggcgagccc     120
gcctccatct cctgccgctc ctcccagtcc ctgttccact ccaagggcaa cacctacctg     180
cactggtacc tgcagaagcc cggccagtcc cccaagctgc tgatcaaccg cgtgtccaac     240
cgcttctccg gcgtgcccga ccgcttctcc ggctccggct ccggcaccga cttcaccctg     300
aagatctccc gcgtggaggc cgaggacgtg ggcgtgtact tctgctccca gtccgcccac     360
gtgccctgga ccttcggcgg cggcaccaag gtggagatca ag                        402
```

<210> SEQ ID NO 74
<211> LENGTH: 402
<212> TYPE: DNA
<213> ORGANISM: Artificial Sequence
<220> FEATURE:
<223> OTHER INFORMATION: Synthesized

<400> SEQUENCE: 74

```
atggacatgc gcgtgcccgc ccagctgctg ggcctgctga tgctgtgggt gtccggctcc      60
tccggcgaca tcgtgatgac ccagtccccc ctgtccctgt ccgtgtcccc cggcgagccc     120
gcctccatct cctgccgctc ctcccagtcc ctgttccact ccaagggcaa cacctacctg     180
cactggtacc tgcagaagcc cggccagtcc cccaagctgc tgatctaccg cgtgtccaac     240
cgcttctccg gcgtgcccga ccgcttctcc ggctccggct ccggcaccga cttcaccctg     300
aagatctccc gcgtggaggc cgaggacgtg ggcgtgtact actgctccca gtccgcccac     360
gtgccctgga ccttcggcgg cggcaccaag gtggagatca ag                        402
```

<210> SEQ ID NO 75
<211> LENGTH: 402
<212> TYPE: DNA
<213> ORGANISM: Artificial Sequence

```
<220> FEATURE:
<223> OTHER INFORMATION: Synthesized

<400> SEQUENCE: 75
atggacatgc gcgtgcccgc ccagctgctg ggcctgctga tgctgtgggt gtccggctcc      60
tccggcgacg tggtgatgac ccagtccccc ctgtccctgt ccgtgtcccc cggcgagccc     120
gcctccatct cctgccgctc ctcccagtcc ctgttccact ccaagggcaa cacctacctg     180
cactggtacc tgcagaagcc cggccagtcc ccccagctgc tgatcaaccg cgtgtccaac     240
cgcttctccg gcgtgcccga ccgcttctcc ggctccggct ccggcaccga cttcaccctg     300
aagatctccc gcgtggaggc cgaggacgtg ggcgtgtact tctgctccca gtccgcccac     360
gtgccctgga ccttcggcgg cggcaccaag gtggagatca ag                        402

<210> SEQ ID NO 76
<211> LENGTH: 402
<212> TYPE: DNA
<213> ORGANISM: Artificial Sequence
<220> FEATURE:
<223> OTHER INFORMATION: Synthesized

<400> SEQUENCE: 76
atggacatgc gcgtgcccgc ccagctgctg ggcctgctga tgctgtgggt gtccggctcc      60
tccggcgaca tcgtgatgac ccagtccccc ctgtccctgt ccgtgtcccc cggcgagccc     120
gcctccatct cctgccgctc ctcccagtcc ctgttccact ccaagggcaa cacctacctg     180
cactggtacc tgcagaagcc cggccagtcc ccccagctgc tgatctaccg cgtgtccaac     240
cgcttctccg gcgtgcccga ccgcttctcc ggctccggct ccggcaccga cttcaccctg     300
aagatctccc gcgtggaggc cgaggacgtg ggcgtgtact actgctccca gtccgcccac     360
gtgccctgga ccttcggcgg cggcaccaag gtggagatca ag                        402

<210> SEQ ID NO 77
<211> LENGTH: 321
<212> TYPE: DNA
<213> ORGANISM: Artificial Sequence
<220> FEATURE:
<223> OTHER INFORMATION: Synthesized

<400> SEQUENCE: 77
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                               321

<210> SEQ ID NO 78
<211> LENGTH: 35
<212> TYPE: PRT
<213> ORGANISM: Artificial Sequence
<220> FEATURE:
<223> OTHER INFORMATION: Synthesized

<400> SEQUENCE: 78

Glu Gln Val Thr Asn Val Gly Gly Ala Val Val Thr Gly Val Thr Ala
1               5                   10                  15

Val Ala Gln Lys Thr Val Glu Gly Ala Gly Ser Ile Ala Ala Ala Thr
```

-continued

```
            20              25              30

Gly Phe Val
        35

<210> SEQ ID NO 79
<211> LENGTH: 28
<212> TYPE: PRT
<213> ORGANISM: Artificial Sequence
<220> FEATURE:
<223> OTHER INFORMATION: Synthesized

<400> SEQUENCE: 79

Lys Glu Gln Val Thr Asn Val Gly Gly Ala Val Val Thr Gly Val Thr
1               5               10              15

Ala Val Ala Gln Lys Thr Val Glu Gly Ala Gly Ser
            20              25

<210> SEQ ID NO 80
<211> LENGTH: 405
<212> TYPE: DNA
<213> ORGANISM: Artificial Sequence
<220> FEATURE:
<223> OTHER INFORMATION: Synthesized

<400> SEQUENCE: 80
atgggatgga gctgggtctt tatcttcctc ctgtcaggaa ctgcaggtgt ccattgccag      60
gtccagctgc agcagtctgg acctgagctg gtgaagcctg ggacttcagt gaagatatcc     120
tgcaaggctt ctggctacag cttcacaagc tactatatac actgggtgaa gcagagtcct     180
ggacagggac ttgagtggat tggatggatt tatcctggaa gtggtaatac taagtacagt     240
gagaagttca gggcaaggc cacactgact gcagacacat cctccagcac agcctacatg      300
cagctcagca gcctgacatc tgaggactct gcagtctatt tctgtgcaag agatggttgc     360
tacgggtttg cttactgggg ccaagggact ctggtcactg tctct                     405

<210> SEQ ID NO 81
<211> LENGTH: 135
<212> TYPE: PRT
<213> ORGANISM: Artificial Sequence
<220> FEATURE:
<223> OTHER INFORMATION: Synthesized

<400> SEQUENCE: 81

Met Gly Trp Ser Trp Val Phe Ile Phe Leu Leu Ser Gly Thr Ala Gly
1               5               10              15

Val His Cys Gln Val Gln Leu Gln Gln Ser Gly Pro Glu Leu Val Lys
            20              25              30

Pro Gly Thr Ser Val Lys Ile Ser Cys Lys Ala Ser Gly Tyr Ser Phe
        35              40              45

Thr Ser Tyr Tyr Ile His Trp Val Lys Gln Ser Pro Gly Gln Gly Leu
    50              55              60

Glu Trp Ile Gly Trp Ile Tyr Pro Gly Ser Gly Asn Thr Lys Tyr Ser
65              70              75              80

Glu Lys Phe Lys Gly Lys Ala Thr Leu Thr Ala Asp Thr Ser Ser Ser
            85              90              95

Thr Ala Tyr Met Gln Leu Ser Ser Leu Thr Ser Glu Asp Ser Ala Val
            100             105             110

Tyr Phe Cys Ala Arg Asp Gly Cys Tyr Gly Phe Ala Tyr Trp Gly Gln
        115             120             125
```

```
Gly Thr Leu Val Thr Val Ser
    130                 135

<210> SEQ ID NO 82
<211> LENGTH: 393
<212> TYPE: DNA
<213> ORGANISM: Artificial Sequence
<220> FEATURE:
<223> OTHER INFORMATION: Synthesized

<400> SEQUENCE: 82
atggagacag acacactcct gttatgggtg ctgctgctct gggttccagg ctccactggt      60
gacattgtgc tgacccaatc tccagcttct ttggctgtgt ctctagggca gagggccacc     120
atctcctgca aggccagcca aagtgttgat tatgatggtg atagttatat gaactggtac     180
caacagaaac caggacagcc acccaaattc ctcatctgtg ctgcatccaa tctagaatct     240
gggatcccag ccaggtttag tggcagtggg tctgggacag acttcaccct caacatccat     300
cctgtggagg aggaggatgc tgcaacctat tactgtcagc aaagtaatga ggatccattc     360
acgttcggct cggggacaaa gttggaaata aaa                                  393

<210> SEQ ID NO 83
<211> LENGTH: 131
<212> TYPE: PRT
<213> ORGANISM: Artificial Sequence
<220> FEATURE:
<223> OTHER INFORMATION: Synthesized

<400> SEQUENCE: 83

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Met Asn Trp Tyr Gln Gln Lys Pro
    50                  55                  60

Gly Gln Pro Pro Lys Phe Leu Ile Cys Ala Ala Ser Asn Leu Glu Ser
65                  70                  75                  80

Gly Ile Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
                100                 105                 110

Gln Gln Ser Asn Glu Asp Pro Phe Thr Phe Gly Ser Gly Thr Lys Leu
            115                 120                 125

Glu Ile Lys
    130

<210> SEQ ID NO 84
<211> LENGTH: 345
<212> TYPE: DNA
<213> ORGANISM: Artificial Sequence
<220> FEATURE:
<223> OTHER INFORMATION: Synthesized

<400> SEQUENCE: 84
gtccagctgc agcagtctgg acctgagctg gtgaagcctg ggacttcagt gaagatatcc      60
tgcaaggctt ctggctacag cttcacaagc tactatatac actgggtgaa gcagagtcct     120
ggacagggac ttgagtggat tggatggatt tatcctggaa gtggtaatac taagtacagt     180
```
gagaagttca agggcaaggc cacactgact gcagacacat cctccagcac agcctacatg    240
cagctcagca gcctgacatc tgaggactct gcagtctatt tctgtgcaag agatggttgc    300
tacgggtttg cttactgggg ccaagggact ctggtcactg tctct    345

<210> SEQ ID NO 85
<211> LENGTH: 115
<212> TYPE: PRT
<213> ORGANISM: Artificial Sequence
<220> FEATURE:
<223> OTHER INFORMATION: Synthesized

<400> SEQUENCE: 85

Val Gln Leu Gln Gln Ser Gly Pro Glu Leu Val Lys Pro Gly Thr Ser
1               5                   10                  15

Val Lys Ile Ser Cys Lys Ala Ser Gly Tyr Ser Phe Thr Ser Tyr Tyr
            20                  25                  30

Ile His Trp Val Lys Gln Ser Pro Gly Gln Gly Leu Glu Trp Ile Gly
        35                  40                  45

Trp Ile Tyr Pro Gly Ser Gly Asn Thr Lys Tyr Ser Glu Lys Phe Lys
    50                  55                  60

Gly Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95

Arg Asp Gly Cys Tyr Gly Phe Ala Tyr Trp Gly Gln Gly Thr Leu Val
            100                 105                 110

Thr Val Ser
        115

<210> SEQ ID NO 86
<211> LENGTH: 333
<212> TYPE: DNA
<213> ORGANISM: Artificial Sequence
<220> FEATURE:
<223> OTHER INFORMATION: Synthesized

<400> SEQUENCE: 86
gacattgtgc tgacccaatc tccagcttct ttggctgtgt ctctagggca gagggccacc    60
atctcctgca aggccagcca aagtgttgat tatgatggtg atagttatat gaactggtac    120
caacagaaac aggacagcc acccaaattc ctcatctgtg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccattc    300
acgttcggct cggggacaaa gttggaaata aaa    333

<210> SEQ ID NO 87
<211> LENGTH: 111
<212> TYPE: PRT
<213> ORGANISM: Artificial Sequence
<220> FEATURE:
<223> OTHER INFORMATION: Synthesized

<400> SEQUENCE: 87

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

```
Gly Asp Ser Tyr Met Asn Trp Tyr Gln Gln Lys Pro Gly Gln Pro Pro
        35                  40                  45

Lys Phe Leu Ile Cys Ala Ala Ser Asn Leu Glu Ser Gly Ile Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Phe Thr Phe Gly Ser Gly Thr Lys Leu Glu Ile Lys
                100                 105                 110

<210> SEQ ID NO 88
<211> LENGTH: 5
<212> TYPE: PRT
<213> ORGANISM: Artificial Sequence
<220> FEATURE:
<223> OTHER INFORMATION: Synthesized

<400> SEQUENCE: 88

Ser Tyr Tyr Ile His
1               5

<210> SEQ ID NO 89
<211> LENGTH: 17
<212> TYPE: PRT
<213> ORGANISM: Artificial Sequence
<220> FEATURE:
<223> OTHER INFORMATION: Synthesized

<400> SEQUENCE: 89

Trp Ile Tyr Pro Gly Ser Gly Asn Thr Lys Tyr Ser Glu Lys Phe Lys
1               5                   10                  15

Gly

<210> SEQ ID NO 90
<211> LENGTH: 8
<212> TYPE: PRT
<213> ORGANISM: Artificial Sequence
<220> FEATURE:
<223> OTHER INFORMATION: Synthesized

<400> SEQUENCE: 90

Asp Gly Cys Tyr Gly Phe Ala Tyr
1               5

<210> SEQ ID NO 91
<211> LENGTH: 15
<212> TYPE: PRT
<213> ORGANISM: Artificial Sequence
<220> FEATURE:
<223> OTHER INFORMATION: Synthesized

<400> SEQUENCE: 91

Lys Ala Ser Gln Ser Val Asp Tyr Asp Gly Asp Ser Tyr Met Asn
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: Synthesized

<400> SEQUENCE: 92
```

```
Ala Ala Ser Asn Leu Glu Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Synthesized

<400> SEQUENCE: 93

Gln Gln Ser Asn Glu Asp Pro Phe Thr
1               5

<210> SEQ ID NO 94
<211> LENGTH: 351
<212> TYPE: DNA
<213> ORGANISM: Artificial Sequence
<220> FEATURE:
<223> OTHER INFORMATION: Synthesized

<400> SEQUENCE: 94
caggtgcagc tggtgcagtc cggcgccgag ctgaagaagc ccggcgcctc cgtgaaggtg      60
tcctgcaagg cctccggcta ctccttcacc tcctactaca tccactgggt gaagcaggcc     120
cccggccagg gcctggagtg gatcggctgg atctaccccg gctccggcaa caccaagtac     180
tccgagaagt tcaagggccg cgccaccctg accgccgaca cctccacctc caccgcctac     240
atggagctgc gctccctgcg ctccgacgac accgccgtgt acttctgcgc cgcgacggc      300 tgctacggct cgcctactg gggccagggc accctggtga ccgtgtcctc a               351

<210> SEQ ID NO 95
<211> LENGTH: 117
<212> TYPE: PRT
<213> ORGANISM: Artificial Sequence
<220> FEATURE:
<223> OTHER INFORMATION: Synthesized

<400> SEQUENCE: 95

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Ser Phe Thr Ser Tyr
                20                  25                  30

Tyr Ile His Trp Val Lys Gln Ala Pro Gly Gln Gly Leu Glu Trp Ile
            35                  40                  45

Gly Trp Ile Tyr Pro Gly Ser Gly Asn Thr Lys Tyr Ser Glu Lys Phe
        50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Cys Tyr Gly Phe Ala Tyr Trp Gly Gln Gly Thr Leu
            100                 105                 110

Val Thr Val Ser Ser
        115

<210> SEQ ID NO 96
<211> LENGTH: 351
<212> TYPE: DNA
<213> ORGANISM: Artificial Sequence
<220> FEATURE:
<223> OTHER INFORMATION: Synthesized
```

-continued

<400> SEQUENCE: 96
caggtgcagc tggtgcagtc cggcgccgag gtgaagaagc ccggcgcctc cgtgaaggtg        60
tcctgcaagg cctccggcta ctccttcacc tcctactaca tccactgggt gcgccaggcc       120
cccggccagg gctggagtg gatcggctgg atctaccccg gctccggcaa caccaagtac        180
tccgagaagt tcaagggccg cgccaccctg accgccgaca cctccacctc caccgcctac       240
atggagctgc gctccctgcg ctccgacgac accgccgtgt acttctgcgc cgcgacggc        300 tgctacggct cgcctactg gggccagggc accctggtga ccgtgtcctc a                351

<210> SEQ ID NO 97
<211> LENGTH: 117
<212> TYPE: PRT
<213> ORGANISM: Artificial Sequence
<220> FEATURE:
<223> OTHER INFORMATION: Synthesized

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Ser Gly Asn Thr Lys Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Cys Tyr Gly Phe Ala Tyr Trp Gly Gln Gly Thr Leu
            100                 105                 110

Val Thr Val Ser Ser
        115

<210> SEQ ID NO 98
<211> LENGTH: 351
<212> TYPE: DNA
<213> ORGANISM: Artificial Sequence
<220> FEATURE:
<223> OTHER INFORMATION: Synthesized

<400> SEQUENCE: 98
caggtgcagc tggtgcagtc cggcgccgag gtgaagaagc ccggcgcctc cgtgaaggtg        60
tcctgcaagg cctccggcta caccttcacc tcctactaca tccactgggt gcgccaggcc       120
cccggccagg gctggagtg gatgggctgg atctaccccg gctccggcaa caccaagtac        180
tccgagaagt tcaagggccg cgccaccatg accgccgaca cctccacctc caccgcctac       240
atggagctgc gctccctgcg ctccgacgac accgccgtgt actactgcgc cgcgacggc        300 tgctacggct cgcctactg gggccagggc accctggtga ccgtgtcctc a                351

<210> SEQ ID NO 99
<211> LENGTH: 117
<212> TYPE: PRT
<213> ORGANISM: Artificial Sequence
<220> FEATURE:
<223> OTHER INFORMATION: Synthesized

<400> SEQUENCE: 99

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
            100                 105                 110

Val Thr Val Ser Ser
        115
```

```
<210> SEQ ID NO 100
<211> LENGTH: 351
<212> TYPE: DNA
<213> ORGANISM: Artificial Sequence
<220> FEATURE:
<223> OTHER INFORMATION: Synthesized
```

<400> SEQUENCE: 100

```
caggtgcagc tggtgcagtc cggcgccgag gtgaagaagc ccggcgcctc cgtgaaggtg       60
tcctgcaagg cctccggcta ctccttcacc tcctactaca tccactgggt gcgccaggcc      120
cccggccagg gctggagtg gatcggctgg atctaccccg gctccggcaa caccaagtac       180
tccgagaagt tcaagggccg cgccaccctg accgccgaca cctccacctc caccgcctac      240
atggagctgc gctccctgcg ctccgacgac accgccgtgt acttctgcgc cgcgacggc       300 tcctacggct cgcctactg gggccagggc accctggtga ccgtgtcctc a                351
```

```
<210> SEQ ID NO 101
<211> LENGTH: 117
<212> TYPE: PRT
<213> ORGANISM: Artificial Sequence
<220> FEATURE:
<223> OTHER INFORMATION: Synthesized
```

<400> SEQUENCE: 101

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Ser Gly Asn Thr Lys Tyr Ser Glu Lys Phe
    50                  55                  60

Lys Gly Arg Ala Thr Leu Thr Ala Asp Thr Ser Thr Ser Thr Ala Tyr
65                  70                  75                  80

Met Glu Leu Arg Ser Leu Arg Ser Asp Asp Thr Ala Val Tyr Phe Cys
                85                  90                  95

Ala Arg Asp Gly Ser Tyr Gly Phe Ala Tyr Trp Gly Gln Gly Thr Leu
            100                 105                 110
```

-continued

```
Val Thr Val Ser Ser
        115

<210> SEQ ID NO 102
<211> LENGTH: 351
<212> TYPE: DNA
<213> ORGANISM: Artificial Sequence
<220> FEATURE:
<223> OTHER INFORMATION: Synthesized

<400> SEQUENCE: 102
caggtgcagc tggtgcagtc cggcgccgag gtgaagaagc ccggcgcctc cgtgaaggtg      60
tcctgcaagg cctccggcta caccttcacc tcctactaca tccactgggt gcgccaggcc     120
cccggccagg gcctggagtg gatgggctgg atctaccccg gctccggcaa caccaagtac     180
tccgagaagt tcaagggccg cgccaccatg accgccgaca cctccacctc caccgcctac     240
atggagctgc gctccctgcg ctccgacgac accgccgtgt actactgcgc ccgcgacggc     300
tcctacggct cgcctactg gggccagggc accctggtga ccgtgtcctc a               351

<210> SEQ ID NO 103
<211> LENGTH: 117
<212> TYPE: PRT
<213> ORGANISM: Artificial Sequence
<220> FEATURE:
<223> OTHER INFORMATION: Synthesized

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Ser Tyr Gly Phe Ala Tyr Trp Gly Gln Gly Thr Leu
            100                 105                 110

Val Thr Val Ser Ser
        115

<210> SEQ ID NO 104
<211> LENGTH: 57
<212> TYPE: DNA
<213> ORGANISM: Artificial Sequence
<220> FEATURE:
<223> OTHER INFORMATION: Synthesized

<400> SEQUENCE: 104
atggagttcg gcctgtcctg gctgttcctg gtggccatcc tgaagggcgt gcagtgc         57

<210> SEQ ID NO 105
<211> LENGTH: 19
<212> TYPE: PRT
<213> ORGANISM: Artificial Sequence
<220> FEATURE:
<223> OTHER INFORMATION: Synthesized
```

<400> SEQUENCE: 105

Met Glu Phe Gly Leu Ser Trp Leu Phe Leu Val Ala Ile Leu Lys Gly
1               5                   10                  15

Val Gln Cys

<210> SEQ ID NO 106
<211> LENGTH: 57
<212> TYPE: DNA
<213> ORGANISM: Artificial Sequence
<220> FEATURE:
<223> OTHER INFORMATION: Synthesized

<400> SEQUENCE: 106
atggactgga cctggagcat cctttttcttg gtggcagcag caacaggtgc ccactcc        57

<210> SEQ ID NO 107
<211> LENGTH: 19
<212> TYPE: PRT
<213> ORGANISM: Artificial Sequence
<220> FEATURE:
<223> OTHER INFORMATION: Synthesized

<400> SEQUENCE: 107

Met Asp Trp Thr Trp Ser Ile Leu Phe Leu Val Ala Ala Ala Thr Gly
1               5                   10                  15

Ala His Ser

<210> SEQ ID NO 108
<211> LENGTH: 333
<212> TYPE: DNA
<213> ORGANISM: Artificial Sequence
<220> FEATURE:
<223> OTHER INFORMATION: Synthesized

<400> SEQUENCE: 108
gacatccagc tgacccagtc cccctcctcc ctgtccgcct ccgtgggcga ccgcgtgacc        60
atcacctgca aggcctccca gtccgtggac tacgacggcg actcctacat gaactggtac       120
cagcagaagc ccggcaaggc ccccaagttc ctgatctgcg ccgcctccaa cctggagtcc       180
ggcgtgccct cccgcttctc cggctccggc tccggcaccg acttcaccct gaccatctcc       240
tccctgcagc ccgaggacgc cgccacctac tactgccagc agtccaacga ggaccccttc       300
accttcggcc agggcaccaa gctggagatc aag                                    333

<210> SEQ ID NO 109
<211> LENGTH: 111
<212> TYPE: PRT
<213> ORGANISM: Artificial Sequence
<220> FEATURE:
<223> OTHER INFORMATION: Synthesized

<400> SEQUENCE: 109

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Phe Leu Ile Cys Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser

```
65                70                75                80

Ser Leu Gln Pro Glu Asp Ala Ala Thr Tyr Tyr Cys Gln Gln Ser Asn
                85                90                95

Glu Asp Pro Phe Thr Phe Gly Gln Gly Thr Lys Leu Glu Ile Lys
            100               105               110
```

<210> SEQ ID NO 110
<211> LENGTH: 333
<212> TYPE: DNA
<213> ORGANISM: Artificial Sequence
<220> FEATURE:
<223> OTHER INFORMATION: Synthesized

<400> SEQUENCE: 110

```
gacatccagc tgacccagtc ccctcctcc  ctgtccgcct ccgtgggcga ccgcgtgacc    60
atcacctgca aggcctccca gtccgtggac tacgacggcg actcctacat gaactggtac   120
cagcagaagc ccggcaaggc ccccaagttc ctgatctacg ccgcctccaa cctggagtcc   180
ggcgtgccct cccgcttctc cggctccggc tccggcaccg acttcaccct gaccatctcc   240
tccctgcagc ccgaggacgc cgccacctac tactgccagc agtccaacga ggaccccttc   300
accttcggcc agggcaccaa gctggagatc aag                               333
```

<210> SEQ ID NO 111
<211> LENGTH: 111
<212> TYPE: PRT
<213> ORGANISM: Artificial Sequence
<220> FEATURE:
<223> OTHER INFORMATION: Synthesized

<400> SEQUENCE: 111

```
Asp Ile Gln Leu Thr Gln Ser Pro Ser Ser Leu Ser Ala Ser Val Gly
1                 5                 10                15

Asp Arg Val Thr Ile Thr Cys Lys Ala Ser Gln Ser Val Asp Tyr Asp
                20                25                30

Gly Asp Ser Tyr Met Asn Trp Tyr Gln Gln Lys Pro Gly Lys Ala Pro
            35                40                45

Lys Phe Leu Ile Tyr Ala Ala Ser Asn Leu Glu Ser Gly Val Pro Ser
    50                55                60

Arg Phe Ser Gly Ser Gly Ser Gly Thr Asp Phe Thr Leu Thr Ile Ser
65                70                75                80

Ser Leu Gln Pro Glu Asp Ala Ala Thr Tyr Tyr Cys Gln Gln Ser Asn
                85                90                95

Glu Asp Pro Phe Thr Phe Gly Gln Gly Thr Lys Leu Glu Ile Lys
            100               105               110
```

<210> SEQ ID NO 112
<211> LENGTH: 333
<212> TYPE: DNA
<213> ORGANISM: Artificial Sequence
<220> FEATURE:
<223> OTHER INFORMATION: Synthesized

<400> SEQUENCE: 112

```
gacatccagc tgacccagtc ccctcctcc  ctgtccgcct ccgtgggcga ccgcgtgacc    60
atcacctgca aggcctccca gtccgtggac tacgacggcg actcctacat gaactggtac   120
cagcagaagc ccggcaaggc ccccaagttc ctgatctgcg ccgcctccaa cctggagtcc   180
ggcgtgccct cccgcttctc cggctccggc tccggcaccg acttcaccct gaccatctcc   240
```

-continued tccctgcagc cgaggactt cgccacctac tactgccagc agtccaacga ggacccttc         300 accttcggcc agggcaccaa gctggagatc aag                                     333

<210> SEQ ID NO 113
<211> LENGTH: 111
<212> TYPE: PRT
<213> ORGANISM: Artificial Sequence
<220> FEATURE:
<223> OTHER INFORMATION: Synthesized

<400> SEQUENCE: 113

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Phe Leu Ile Cys Ala Ala Ser Asn Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 114
<211> LENGTH: 333
<212> TYPE: DNA
<213> ORGANISM: Artificial Sequence
<220> FEATURE:
<223> OTHER INFORMATION: Synthesized

<400> SEQUENCE: 114
gacatccagc tgacccagtc cccctcctcc ctgtccgcct ccgtgggcga ccgcgtgacc          60
atcacctgca aggcctccca gtccgtggac tacgacggcg actcctacat gaactggtac         120
cagcagaagc ccggcaaggc ccccaagttc ctgatctacg ccgcctccaa cctggagtcc         180
ggcgtgccct cccgcttctc cggctccggc tccggcaccg acttcaccct gaccatctcc         240
tccctgcagc cgaggactt cgccacctac tactgccagc agtccaacga ggacccttc          300 accttcggcc agggcaccaa gctggagatc aag                                     333

<210> SEQ ID NO 115
<211> LENGTH: 111
<212> TYPE: PRT
<213> ORGANISM: Artificial Sequence
<220> FEATURE:
<223> OTHER INFORMATION: Synthesized

<400> SEQUENCE: 115

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Phe Leu Ile Tyr Ala Ala Ser Asn Leu Glu Ser Gly Val Pro Ser
        50                  55                  60

```
Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 116
<211> LENGTH: 66
<212> TYPE: DNA
<213> ORGANISM: Artificial Sequence
<220> FEATURE:
<223> OTHER INFORMATION: Synthesized

<400> SEQUENCE: 116
atggacatgc gcgtgcccgc ccagctgctg ggcctgctga tgctgtgggt gtccggctcc      60
tccggc                                                                  66

<210> SEQ ID NO 117
<211> LENGTH: 117
<212> TYPE: PRT
<213> ORGANISM: Artificial Sequence
<220> FEATURE:
<223> OTHER INFORMATION: Synthesized

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
                20                  25                  30

Gly Ile Ser Trp Val Arg Gln Ala Pro Gly Gln Gly Leu Glu Trp Met
            35                  40                  45

Gly Trp Ile Ser Pro Tyr Asn Gly Asp Thr Asn Tyr Ala Gln Asn Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Gly Ser Met Ser Asp Tyr Trp Gly Gln Gly Thr Leu
            100                 105                 110

Val Thr Val Ser Ser
        115

<210> SEQ ID NO 118
<211> LENGTH: 107
<212> TYPE: PRT
<213> ORGANISM: Artificial Sequence
<220> FEATURE:
<223> OTHER INFORMATION: Synthesized

<400> SEQUENCE: 118

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Pro
                85                  90                  95

Thr Phe Gly Gln Gly Thr Lys Leu Glu Ile Lys
            100                 105
```

<210> SEQ ID NO 119
<211> LENGTH: 117
<212> TYPE: PRT
<213> ORGANISM: Artificial Sequence
<220> FEATURE:
<223> OTHER INFORMATION: Synthesized

<400> SEQUENCE: 119

```
Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Ser Phe Thr Ser Tyr
                20                  25                  30

Tyr Ile His Trp Val Arg Gln Ala Pro Gly Gln Gly Leu Glu Trp Met
            35                  40                  45

Gly Trp Ile Tyr Pro Gly Ser Gly Asn Thr Lys Tyr Ser Glu Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
                100                 105                 110

Val Thr Val Ser Ser
        115
```

<210> SEQ ID NO 120
<211> LENGTH: 111
<212> TYPE: PRT
<213> ORGANISM: Artificial Sequence
<220> FEATURE:
<223> OTHER INFORMATION: Synthesized

<400> SEQUENCE: 120

```
Asp Ile Gln Leu Thr Gln Ser Pro Ser Ser Leu Ser Ala Ser Val Gly
1                   5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Ala Ser Asn Leu Glu Ser Gly Val Pro Ser
        50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys
                100                 105                 110
```

<210> SEQ ID NO 121
<211> LENGTH: 117
<212> TYPE: PRT
<213> ORGANISM: Artificial Sequence

```
<220> FEATURE:
<223> OTHER INFORMATION: Synthesized
<220> FEATURE:
<221> NAME/KEY: VARIANT
<222> LOCATION: (11)..(11)
<223> OTHER INFORMATION: Xaa = V or L
<220> FEATURE:
<221> NAME/KEY: VARIANT
<222> LOCATION: (28)..(28)
<223> OTHER INFORMATION: Xaa = S or T
<220> FEATURE:
<221> NAME/KEY: VARIANT
<222> LOCATION: (38)..(38)
<223> OTHER INFORMATION: Xaa = R or K
<220> FEATURE:
<221> NAME/KEY: VARIANT
<222> LOCATION: (48)..(48)
<223> OTHER INFORMATION: Xaa = M or I
<220> FEATURE:
<221> NAME/KEY: VARIANT
<222> LOCATION: (68)..(68)
<223> OTHER INFORMATION: Xaa = V or A
<220> FEATURE:
<221> NAME/KEY: VARIANT
<222> LOCATION: (70)..(70)
<223> OTHER INFORMATION: Xaa = M or L
<220> FEATURE:
<221> NAME/KEY: VARIANT
<222> LOCATION: (72)..(72)
<223> OTHER INFORMATION: Xaa = T or A
<220> FEATURE:
<221> NAME/KEY: VARIANT
<222> LOCATION: (95)..(95)
<223> OTHER INFORMATION: Xaa = Y or F
<220> FEATURE:
<221> NAME/KEY: VARIANT
<222> LOCATION: (101)..(101)
<223> OTHER INFORMATION: Xaa = C or S

<400> SEQUENCE: 121

Gln Val Gln Leu Val Gln Ser Gly Ala Glu Xaa Lys Lys Pro Gly Ala
1               5                   10                  15

Ser Val Lys Val Ser Cys Lys Ala Ser Gly Tyr Xaa Phe Thr Ser Tyr
            20                  25                  30

Tyr Ile His Trp Val Xaa Gln Ala Pro Gly Gln Gly Leu Glu Trp Xaa
        35                  40                  45

Gly Trp Ile Tyr Pro Gly Ser Gly Asn Thr Lys Tyr Ser Glu Lys Phe
    50                  55                  60

Lys Gly Arg Xaa Thr Xaa Thr Xaa Asp Thr Ser Thr Ser Thr Ala Tyr
65                  70                  75                  80

Met Glu Leu Arg Ser Leu Arg Ser Asp Asp Thr Ala Val Tyr Xaa Cys
                85                  90                  95

Ala Arg Asp Gly Xaa Tyr Gly Phe Ala Tyr Trp Gly Gln Gly Thr Leu
            100                 105                 110

Val Thr Val Ser Ser
        115

<210> SEQ ID NO 122
<211> LENGTH: 111
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (50)..(50)
<223> OTHER INFORMATION: Xaa = L or F
<220> FEATURE:
<221> NAME/KEY: VARIANT
<222> LOCATION: (53)..(53)
```

```
<223> OTHER INFORMATION: Xaa = Y or C
<220> FEATURE:
<221> NAME/KEY: VARIANT
<222> LOCATION: (87)..(87)
<223> OTHER INFORMATION: Xaa = F or A

<400> SEQUENCE: 122

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Xaa Leu Ile Xaa Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Xaa Ala Thr Tyr Tyr Cys Gln Gln Ser Asn
                85                  90                  95

Glu Asp Pro Phe Thr Phe Gly Gln Gly Thr Lys Leu Glu Ile Lys
            100                 105                 110

<210> SEQ ID NO 123
<211> LENGTH: 8
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (3)..(3)
<223> OTHER INFORMATION: Xaa = C or M or S or T

<400> SEQUENCE: 123

Asp Gly Xaa Tyr Gly Phe Ala Tyr
1               5

<210> SEQ ID NO 124
<211> LENGTH: 218
<212> TYPE: PRT
<213> ORGANISM: Artificial Sequence
<220> FEATURE:
<223> OTHER INFORMATION: Synthesized

<400> SEQUENCE: 124

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Phe Leu Ile Cys Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

-continued

```
Leu Lys Ser Gly Thr Ala Ser Val Val Cys Leu Leu Asn Asn Phe Tyr
    130             135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
    210                 215
```

<210> SEQ ID NO 125
<211> LENGTH: 217
<212> TYPE: PRT
<213> ORGANISM: Artificial Sequence
<220> FEATURE:
<223> OTHER INFORMATION: Synthesized

<400> SEQUENCE: 125

```
Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
                35                  40                  45

Lys Phe Leu Ile Cys Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Phe Thr Phe Gly Gln Gly Thr Lys Leu Glu Ile Lys Thr
                100                 105                 110

Val Ala Ala Pro Ser Val Phe Ile Phe Pro Pro Ser Asp Glu Gln Leu
                115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
                195                 200                 205

Thr Lys Ser Phe Asn Arg Gly Glu Cys
    210                 215
```

<210> SEQ ID NO 126
<211> LENGTH: 447
<212> TYPE: PRT
<213> ORGANISM: Artificial Sequence
<220> FEATURE:
<223> OTHER INFORMATION: Synthesized

<400> SEQUENCE: 126

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Ile His Trp Val Arg Gln Ala Pro Gly Gln Gly Leu Glu Trp Met
            35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Val Lys
            275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415
```

-continued

```
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 127
<211> LENGTH: 447
<212> TYPE: PRT
<213> ORGANISM: Artificial Sequence
<220> FEATURE:
<223> OTHER INFORMATION: Synthesized

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Ile Tyr Pro Gly Ser Gly Asn Thr Lys Tyr Ser Glu Lys Phe
    50                  55                  60

Lys Gly Arg Ala Thr Met Thr Ala Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Cys Tyr Gly Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Arg Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

-continued

```
Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                    405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 128
<211> LENGTH: 326
<212> TYPE: PRT
<213> ORGANISM: Artificial Sequence
<220> FEATURE:
<223> OTHER INFORMATION: Synthesized

<400> SEQUENCE: 128

Ala Ser Thr Lys Gly Pro Ser Val Phe Pro Leu Ala Pro Cys Ser Arg
1                   5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                    85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                    165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                    245                 250                 255
```

```
Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 129
<211> LENGTH: 330
<212> TYPE: PRT
<213> ORGANISM: Artificial Sequence
<220> FEATURE:
<223> OTHER INFORMATION: Synthesized

<400> SEQUENCE: 129

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 130
<211> LENGTH: 113
<212> TYPE: PRT
<213> ORGANISM: Artificial sequence
<220> FEATURE:
<223> OTHER INFORMATION: Synthesized

<400> SEQUENCE: 130
```

```
Glu Val Gln Leu Val Gln Ser Gly Gly Gly Leu Val Glu Pro Gly Gly
1               5                   10                  15

Ser Leu Arg Leu Ser Cys Ala Val Ser Gly Phe Asp Phe Glu Lys Ala
            20                  25                  30

Trp Met Ser Trp Val Arg Gln Ala Pro Gly Gln Gly Leu Gln Trp Val
        35                  40                  45

Ala Arg Ile Lys Ser Thr Ala Asp Gly Gly Thr Thr Ser Tyr Ala Ala
    50                  55                  60

Pro Val Glu Gly Arg Phe Ile Ile Ser Arg Asp Asp Ser Arg Asn Met
65                  70                  75                  80

Leu Tyr Leu Gln Met Asn Ser Leu Lys Thr Glu Asp Thr Ala Val Tyr
                85                  90                  95

Tyr Cys Thr Ser Ala His Trp Gly Gln Gly Thr Leu Val Thr Val Ser
            100                 105                 110

Ser
```

```
<210> SEQ ID NO 131
<211> LENGTH: 5
<212> TYPE: PRT
<213> ORGANISM: Artificial sequence
<220> FEATURE:
<223> OTHER INFORMATION: Synthesized

<400> SEQUENCE: 131
```

```
Lys Ala Trp Met Ser
1               5
```

```
<210> SEQ ID NO 132
<211> LENGTH: 19
<212> TYPE: PRT
<213> ORGANISM: Artificial sequence
<220> FEATURE:
<223> OTHER INFORMATION: Synthesized

<400> SEQUENCE: 132
```

```
Arg Ile Lys Ser Thr Ala Asp Gly Gly Thr Thr Ser Tyr Ala Ala Pro
1               5                   10                  15

Val Glu Gly
```

```
<210> SEQ ID NO 133

<400> SEQUENCE: 133

000
```

<210> SEQ ID NO 134
<211> LENGTH: 108
<212> TYPE: PRT
<213> ORGANISM: Artificial sequence
<220> FEATURE:
<223> OTHER INFORMATION: Synthesized

<400> SEQUENCE: 134

Gln Ser Val Leu Thr Gln Pro Pro Ser Val Ser Val Ser Pro Gly Gln
1               5                   10                  15

Thr Ala Arg Ile Thr Cys Ser Gly Glu Ala Leu Pro Met Gln Phe Ala
            20                  25                  30

His Trp Tyr Gln Gln Arg Pro Gly Lys Ala Pro Val Ile Val Val Tyr
        35                  40                  45

Lys Asp Ser Glu Arg Pro Ser Gly Val Pro Glu Arg Phe Ser Gly Ser
    50                  55                  60

Ser Ser Gly Thr Thr Ala Thr Leu Thr Ile Thr Gly Val Gln Ala Glu
65                  70                  75                  80

Asp Glu Ala Asp Tyr Tyr Cys Gln Ser Pro Asp Ser Thr Asn Thr Tyr
                85                  90                  95

Glu Val Phe Gly Gly Gly Thr Lys Leu Thr Val Leu
            100                 105

<210> SEQ ID NO 135
<211> LENGTH: 11
<212> TYPE: PRT
<213> ORGANISM: Artificial sequence
<220> FEATURE:
<223> OTHER INFORMATION: Synthesized

<400> SEQUENCE: 135

Ser Gly Glu Ala Leu Pro Met Gln Phe Ala His
1               5                   10

<210> SEQ ID NO 136
<211> LENGTH: 7
<212> TYPE: PRT
<213> ORGANISM: Artificial sequence
<220> FEATURE:
<223> OTHER INFORMATION: Synthesized

<400> SEQUENCE: 136

Lys Asp Ser Glu Arg Pro Ser
1               5

<210> SEQ ID NO 137
<211> LENGTH: 11
<212> TYPE: PRT
<213> ORGANISM: Artificial sequence
<220> FEATURE:
<223> OTHER INFORMATION: Synthesized

<400> SEQUENCE: 137

Gln Ser Pro Asp Ser Thr Asn Thr Tyr Glu Val
1               5                   10

<210> SEQ ID NO 138
<211> LENGTH: 124
<212> TYPE: PRT
<213> ORGANISM: Artificial sequence
<220> FEATURE:
<223> OTHER INFORMATION: Synthesized

<400> SEQUENCE: 138

```
Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Lys Arg Lys Tyr Ser Gln Lys Phe
    50                  55                  60

Gln Asp Arg Val Thr Ile Asn Arg Asp Thr Ser Ala Ser Thr Ile Tyr
65                  70                  75                  80

Met Glu Leu Ser Ser Leu Gly Ser Glu Asp Thr Ala Val Tyr Tyr Cys
                85                  90                  95

Ala Arg Glu Glu Asp His Ala Gly Ser Gly Ser Tyr Leu Ser Met Asp
            100                 105                 110

Val Trp Gly Gln Gly Thr Leu Val Thr Val Ser Ser
        115                 120
```

<210> SEQ ID NO 139
<211> LENGTH: 5
<212> TYPE: PRT
<213> ORGANISM: Artificial sequence
<220> FEATURE:
<223> OTHER INFORMATION: Synthesized

<400> SEQUENCE: 139

```
Asn Tyr Ala Met His
1               5
```

<210> SEQ ID NO 140
<211> LENGTH: 17
<212> TYPE: PRT
<213> ORGANISM: Artificial sequence
<220> FEATURE:
<223> OTHER INFORMATION: Synthesized

<400> SEQUENCE: 140

```
Trp Ile Asn Ala Gly Asn Gly Lys Arg Lys Tyr Ser Gln Lys Phe Gln
1               5                   10                  15

Asp
```

<210> SEQ ID NO 141
<211> LENGTH: 15
<212> TYPE: PRT
<213> ORGANISM: Artificial sequence
<220> FEATURE:
<223> OTHER INFORMATION: Synthesized

<400> SEQUENCE: 141

```
Glu Glu Asp His Ala Gly Ser Gly Ser Tyr Leu Ser Met Asp Val
1               5                   10                  15
```

<210> SEQ ID NO 142
<211> LENGTH: 113
<212> TYPE: PRT
<213> ORGANISM: Artificial sequence
<220> FEATURE:
<223> OTHER INFORMATION: Synthesized

<400> SEQUENCE: 142

```
Asp Val Val Met Thr Gln Ser Pro Asp Ser Leu Ala Val Ser Leu Gly
1               5                   10                  15

Glu Arg Ala Thr Ile Asn Cys Lys Ser Ser Gln Asn Val Leu Tyr Ser
```

-continued

```
                 20              25              30

Ser Asn Asn Lys Asn Tyr Leu Ala Trp Tyr Gln Gln Lys Pro Gly His
         35              40              45

Pro Pro Lys Leu Leu Ile Tyr Trp Ala Ser Thr Arg Glu Ser Gly Val
     50              55              60

Pro Asp Arg Phe Ser Gly Ser Gly Ser Gly Thr Asp Phe Thr Leu Thr
65              70              75              80

Ile Thr Ser Leu Gln Thr Glu Asp Val Ala Val Tyr Tyr Cys Gln Gln
                 85              90              95

Tyr Tyr Ser Ser Pro Leu Thr Phe Gly Gly Gly Thr Lys Val Glu Ile
             100             105             110

Lys
```

```
<210> SEQ ID NO 143
<211> LENGTH: 17
<212> TYPE: PRT
<213> ORGANISM: Artificial sequence
<220> FEATURE:
<223> OTHER INFORMATION: Synthesized

<400> SEQUENCE: 143

Lys Ser Ser Gln Asn Val Leu Tyr Ser Ser Asn Asn Lys Asn Tyr Leu
1               5               10              15

Ala
```

```
<210> SEQ ID NO 144
<211> LENGTH: 7
<212> TYPE: PRT
<213> ORGANISM: Artificial sequence
<220> FEATURE:
<223> OTHER INFORMATION: Synthesized

<400> SEQUENCE: 144

Trp Ala Ser Thr Arg Glu Ser
1               5
```

```
<210> SEQ ID NO 145
<211> LENGTH: 9
<212> TYPE: PRT
<213> ORGANISM: Artificial sequence
<220> FEATURE:
<223> OTHER INFORMATION: Synthesized

<400> SEQUENCE: 145

Gln Gln Tyr Tyr Ser Ser Pro Leu Thr
1               5
```

```
<210> SEQ ID NO 146
<211> LENGTH: 5
<212> TYPE: PRT
<213> ORGANISM: Artificial sequence
<220> FEATURE:
<223> OTHER INFORMATION: Synthesized

<400> SEQUENCE: 146

Asn Tyr Gly Met Ser
1               5
```

```
<210> SEQ ID NO 147
<211> LENGTH: 17
<212> TYPE: PRT
<213> ORGANISM: Artificial sequence
<220> FEATURE:
```

-continued

```
<223> OTHER INFORMATION: Synthesized

<400> SEQUENCE: 147

Ser Ile Ser Ser Gly Gly Gly Ser Thr Tyr Tyr Pro Asp Asn Val Lys
1               5                   10                  15

Gly

<210> SEQ ID NO 148
<211> LENGTH: 7
<212> TYPE: PRT
<213> ORGANISM: Artificial sequence
<220> FEATURE:
<223> OTHER INFORMATION: Synthesized

<400> SEQUENCE: 148

Gly Gly Ala Gly Ile Asp Tyr
1               5

<210> SEQ ID NO 149
<211> LENGTH: 17
<212> TYPE: PRT
<213> ORGANISM: Artificial sequence
<220> FEATURE:
<223> OTHER INFORMATION: Synthesized

<400> SEQUENCE: 149

Lys Ser Ile Gln Thr Leu Leu Tyr Ser Ser Asn Gln Lys Asn Tyr Leu
1               5                   10                  15

Ala

<210> SEQ ID NO 150
<211> LENGTH: 7
<212> TYPE: PRT
<213> ORGANISM: Artificial sequence
<220> FEATURE:
<223> OTHER INFORMATION: Synthesized

<400> SEQUENCE: 150

Trp Ala Ser Ile Arg Lys Ser
1               5

<210> SEQ ID NO 151
<211> LENGTH: 9
<212> TYPE: PRT
<213> ORGANISM: Artificial sequence
<220> FEATURE:
<223> OTHER INFORMATION: Synthesized

<400> SEQUENCE: 151

Gln Gln Tyr Tyr Ser Tyr Pro Leu Thr
1               5
```